(12) United States Patent
Cho et al.

(10) Patent No.: US 11,559,223 B2
(45) Date of Patent: Jan. 24, 2023

(54) GLUCOSE MEASURING APPARATUS AND METHOD

(71) Applicant: Samsung Electronics Co., Ltd., Gyeonggi-do (KR)

(72) Inventors: Seong-je Cho, Gyeonggi-do (KR); Kwang-bok Kim, Incheon (KR); Sun-tae Jung, Gyeonggi-do (KR); Jae-geol Cho, Gyeonggi-do (KR); Chul-ho Cho, Gyeonggi-do (KR); Seung-min Lee, Seoul (KR); Jeong-gun Lee, Seoul (KR); In-jo Jeong, Gyeonggi-do (KR)

(73) Assignee: Samsung Electronics Co., Ltd

( * ) Notice: Subject to any disclaimer, the term of this patent is extended or adjusted under 35 U.S.C. 154(b) by 344 days.

(21) Appl. No.: 16/752,078

(22) Filed: Jan. 24, 2020

(65) Prior Publication Data
US 2020/0155032 A1    May 21, 2020

Related U.S. Application Data

(62) Division of application No. 14/927,057, filed on Oct. 29, 2015, now abandoned.

(30) Foreign Application Priority Data

Oct. 29, 2014 (KR) .......................... 10-2014-0148447

(51) Int. Cl.
*A61B 5/08* (2006.01)
*A61B 5/00* (2006.01)
(Continued)

(52) U.S. Cl.
CPC .............. *A61B 5/082* (2013.01); *A61B 5/097* (2013.01); *A61B 5/1455* (2013.01);
(Continued)

(58) Field of Classification Search
None
See application file for complete search history.

(56) References Cited

U.S. PATENT DOCUMENTS 4,169,676 A    10/1979    Kaiser
5,028,787 A    7/1991    Rosenthal et al.
(Continued)

FOREIGN PATENT DOCUMENTS

CN    1165556    11/1997
CN    1555242    12/2004
(Continued)

OTHER PUBLICATIONS

Chinese Office Action dated Sep. 1, 2020 issued in counterpart application No. 201580071340.6, 26 pages.
(Continued)

*Primary Examiner* — Jay B Shah
(74) *Attorney, Agent, or Firm* — The Farrell Law Firm, P.C.

(57) ABSTRACT

Disclosed is a glucose measuring apparatus including a pressure measurer having an elastic part or a pressure sensor, that measures a pressure applied to an object, a film that comprises a first optical waveguide configured to be close to the object, a near infrared ray (NIR) irradiator that irradiates an NIR to the first optical waveguide if the measured pressure is greater than or equal to a preset value, an NIR receiver that receives an attenuated total reflection NIR (ATR-NIR) from the first optical waveguide, and an analyzer that measures a blood glucose level based on the ATR-NIR, wherein the film is an independent module that can be combined with and separated from the glucose measuring apparatus.

13 Claims, 20 Drawing Sheets

(51) Int. Cl.
*A61B 5/097* (2006.01)
*A61B 5/145* (2006.01)
*A61B 5/1455* (2006.01)
*G01L 5/00* (2006.01)
*G01N 21/552* (2014.01)

(52) U.S. Cl.
CPC ........ *A61B 5/14532* (2013.01); *A61B 5/6843* (2013.01); *A61B 5/6898* (2013.01); *A61B 5/7278* (2013.01); *A61B 5/7285* (2013.01); *G01L 5/00* (2013.01); *G01N 21/552* (2013.01); *A61B 2560/0431* (2013.01); *A61B 2560/0462* (2013.01); *A61B 2562/0247* (2013.01); *A61B 2562/146* (2013.01); *G01N 2201/061* (2013.01); *G01N 2201/08* (2013.01)

(56) References Cited

U.S. PATENT DOCUMENTS

| | | |
|---|---|---|
| 5,086,229 A | 2/1992 | Rosenthal et al. |
| 5,115,133 A | 5/1992 | Knudson |
| 5,178,142 A | 1/1993 | Harjunmaa et al. |
| 5,179,951 A | 1/1993 | Knudson |
| 5,267,152 A | 11/1993 | Yang et al. |
| 5,313,941 A | 5/1994 | Brag et al. |
| 5,398,681 A | 3/1995 | Kupershmidt |
| 5,433,197 A | 7/1995 | Stark |
| 5,533,509 A | 7/1996 | Koashi et al. |
| 5,626,140 A | 5/1997 | Feldman |
| 6,001,067 A | 12/1999 | Shults et al. |
| 6,147,749 A | 11/2000 | Kubo et al. |
| 6,362,144 B1 | 3/2002 | Berman et al. |
| 6,421,548 B1 | 7/2002 | Berman et al. |
| 6,424,848 B1 | 7/2002 | Berman et al. |
| 6,424,849 B1 | 7/2002 | Berman et al. |
| 6,429,023 B1 | 8/2002 | Gharavi |
| 6,430,424 B1 | 8/2002 | Berman et al. |
| 6,445,938 B1 | 9/2002 | Berman et al. |
| 6,522,903 B1 | 2/2003 | Berman et al. |
| 6,748,250 B1 | 6/2004 | Berman et al. |
| 6,975,891 B2 | 12/2005 | Pawluczyk |
| 7,497,126 B2 | 3/2009 | Tojo et al. |
| 10,911,427 B1 | 2/2021 | Murakami et al. |
| 2002/0151773 A1 | 10/2002 | Berman et al. |
| 2003/0149348 A1 | 8/2003 | Raskas |
| 2003/0176775 A1 | 9/2003 | Berman |
| 2004/0121358 A1 | 6/2004 | Uchida et al. |
| 2005/0171413 A1 | 8/2005 | Blair |
| 2008/0045825 A1 | 2/2008 | Melker et al. |
| 2008/0188724 A1 | 8/2008 | Hwang et al. |
| 2009/0054799 A1 | 2/2009 | Vrtis |
| 2009/0312615 A1 | 12/2009 | Caduff et al. |
| 2010/0249546 A1 | 9/2010 | White |
| 2011/0105867 A1 | 5/2011 | Schultz et al. |
| 2012/0251040 A1* | 10/2012 | Okayama ........... G02B 6/12014 385/14 |
| 2013/0062799 A1* | 3/2013 | Jeong .................... B82Y 10/00 264/1.24 |

FOREIGN PATENT DOCUMENTS

| | | |
|---|---|---|
| EP | 0 801 297 | 10/1997 |
| EP | 1 137 364 | 10/2001 |
| EP | 1 500 369 | 1/2005 |
| JP | 2008-215893 | 9/2008 |
| JP | 2011-102772 | 5/2011 |
| KR | 1020080072158 | 8/2008 |
| KR | 1020080073988 | 8/2008 |
| KR | 1020100054131 | 5/2010 |
| WO | WO 00/21437 | 4/2000 |
| WO | WO 2009/136311 | 11/2009 |

OTHER PUBLICATIONS

Korean Office Action dated Jan. 14, 2021 issued in counterpart application No. 10-2014-148447, 17 pages.
Chinese Office Action dated Mar. 18, 2020 issued in counterpart application No. 201580071340.6, 31 pages.
Byung-Wook Park et al., "Optical Communication and Sensing Modules for Plastic Optical Fibers," Korean Chem. Eng. Res., vol. 47, No. 5, Oct. 2009, pp. 558-564.
Kwang-Take Kim et al., "Low Loss Plastic Optical Fiber Coupler Incorporating Polymer Tapering Waveguide Region," Aug. 9, 2012, 14 pages.
International Search Report dated Feb. 29, 2016 issued in counterpart application No. PCT/KR2015/011407, 15 pages.
European Search Report dated Oct. 13, 2017 issued in counterpart application No. 15853651.6-1657, 9 pages.
Chinese Office Action dated Sep. 2, 2019 issued in counterpart application No. 201580071340.6, 28 pages.

* cited by examiner

FIG. 2
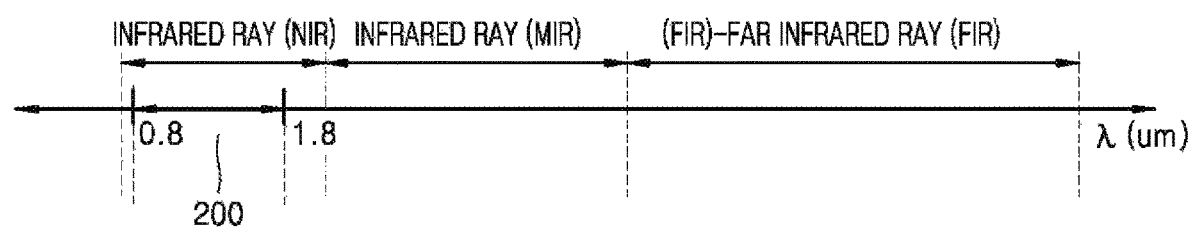
FIG. 3A    FIG. 3B
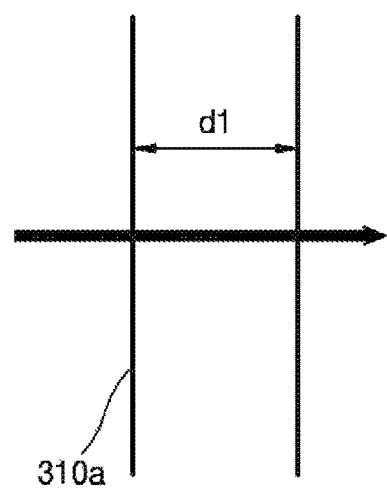
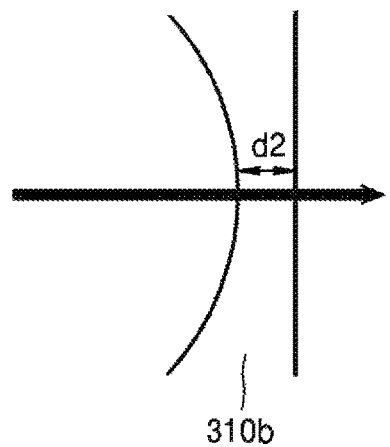

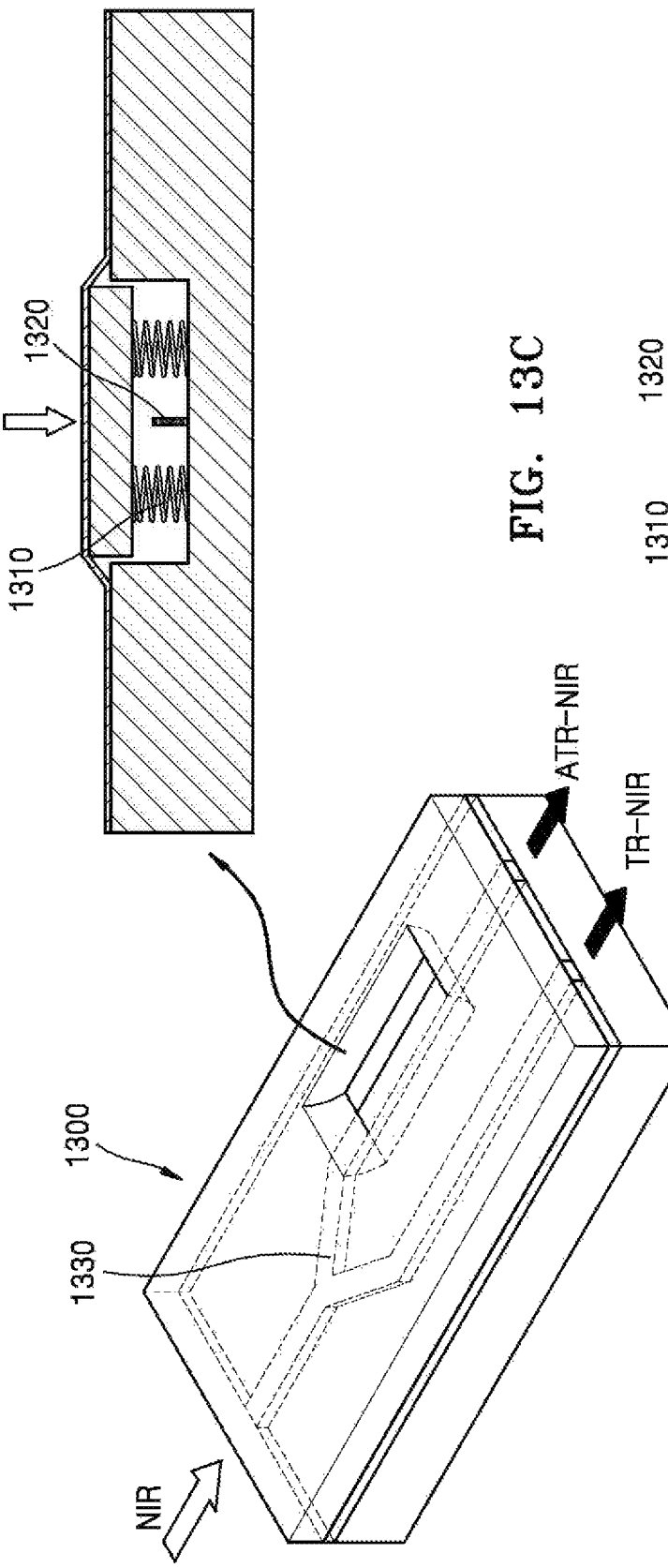
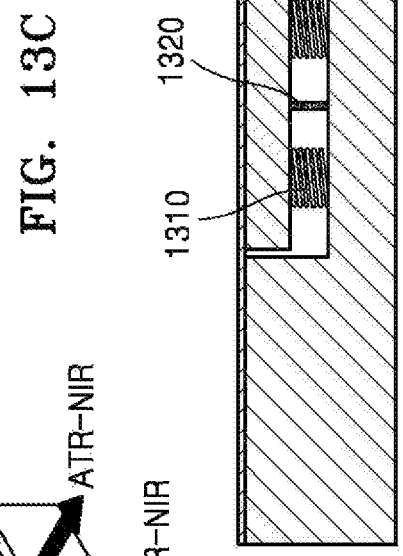
FIG. 13A
FIG. 13B
FIG. 13C

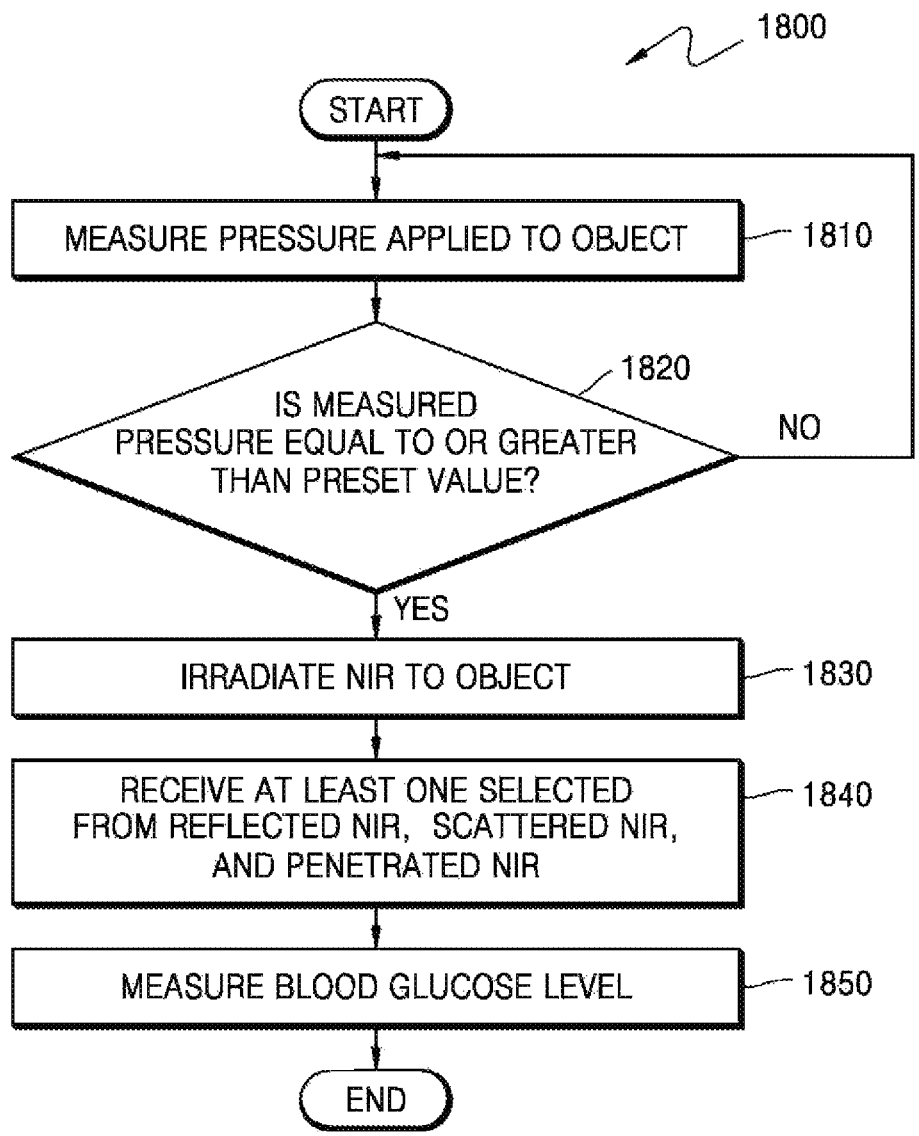

GLUCOSE MEASURING APPARATUS AND METHOD

PRIORITY

This application is a Divisional Application of U.S. patent application Ser. No. 14/927,057, which was filed on Oct. 29, 2015, and claims priority under 35 U.S.C. 119 to Korean Patent Application No. 10-2014-0148447, filed on Oct. 29, 2014 in the Korean Intellectual Property Office, the content of each of which is incorporated herein by reference.

BACKGROUND

1. Field of the Disclosure

The present disclosure relates generally to a glucose measuring apparatus and method, and more particularly, to a noninvasive glucose measuring apparatus and method using infrared ray (IR) technology.

2. Description of the Related Art

An invasive glucose measuring apparatus is used to draw blood from a user through a needle or an injector, for example, in order to measure a blood glucose level. Therefore, the user tends to experience physical pain when the invasive glucose measuring apparatus is used. Furthermore, if the invasive glucose measuring apparatus is not sanitized, the user may be infected with germs, viruses or bacteria.

However, a user does not tend to experience any physical pain when a noninvasive glucose measuring apparatus is used. Examples of noninvasive glucose measuring apparatuses include a glucose measuring apparatus using IR, an electromagnetic field, exhaled breath, or a patch, for example.

The glucose measuring apparatus using IR measures a blood glucose level by irradiating an IR having several wavelengths to a user and analyzing a response of the user to the irradiated IR. However, since other components in addition to glucose are affected by the IR, it is difficult to precisely measure a blood glucose level. Moreover, it is difficult to efficiently measure the blood glucose level via the glucose measuring apparatus using IR due to an error caused by such factors as an external pressure.

Therefore, there is a need in the art for a glucose measuring apparatus and method whereby a user does not experience any pain and a blood glucose level is precisely and efficiently measured by using a noninvasive method.

SUMMARY

The present disclosure has been made to address the above-mentioned problems and disadvantages, and to provide at least the advantages described below.

Accordingly, an aspect of embodiments of the present disclosure is to provide a glucose measuring apparatus and method using infrared ray (IR).

Another aspect of embodiments of the present disclosure is to provide an infrared glucose measuring apparatus that reduces errors occurring due to noise caused by internal components except glucose and an external pressure and a method of measuring glucose by using the apparatus.

Additional aspects will be set forth in part in the description which follows and, in part, will be apparent from the description, or may be learned by practice of the presented exemplary embodiments.

According to an aspect of the present disclosure, a glucose measuring apparatus including a pressure measurer having an elastic part or a pressure sensor, that measures a pressure applied to an object, a film that comprises a first optical waveguide configured to be close to the object, a near infrared ray (NIR) irradiator that irradiates an NIR to the first optical waveguide if the measured pressure is greater than or equal to a preset value, an NIR receiver that receives an attenuated total reflection NIR (ATR-NIR) from the first optical waveguide, and an analyzer that measures a blood glucose level based on the ATR-NIR, wherein the film is an independent module that can be combined with and separated from the glucose measuring apparatus.

According to an aspect of the present disclosure, a method of measuring a blood glucose level includes measuring a pressure applied to an object, if the pressure is greater than or equal to a preset value, irradiating a NIR to a first optical waveguide that is close to the object, receiving an ATR-NIR from the first optical waveguide, and measuring a blood glucose level based on the ATR-NIR, wherein a film including the first optical waveguide is an independent module that can be combined with and separated from the glucose measuring apparatus.

According to an aspect of the present disclosure, a computer program product id disclosed comprising a non-transitory computer-readable storage medium configured to store one or more computer programs including instructions that, when executed by at least one processor, cause the at least one processor to control to perform a method of measuring a blood glucose level in a glucose measuring apparatus, including measuring a pressure applied to an object, if the pressure is greater than or equal to a preset value, irradiating a NIR to a first optical waveguide that is close to the object, receiving an ATR-NIR from the first optical waveguide, and measuring a blood glucose level based on the ATR-NIR, wherein a film including the first optical waveguide is an independent module that can be combined with and separated from the glucose measuring apparatus.

BRIEF DESCRIPTION OF THE DRAWINGS

The above and/or other aspects, features, and advantages of the present disclosure will become apparent and more readily appreciated from the following description of the embodiments, taken in conjunction with the accompanying drawings in which:

FIG. 2 illustrates a wavelength of an NIR irradiated by a glucose measuring apparatus, according to an embodiment of the present disclosure;

FIGS. 3A and 3B illustrate errors occurring due to an external pressure when measuring glucose;

FIGS. 13A, 13B and 13C illustrate a structure of a pressure measurer included in a glucose measuring apparatus, according to an embodiment of the present disclosure;

FIG. 18 is a flowchart of a glucose measuring method according to an embodiment of the present disclosure;

DETAILED DESCRIPTION

Figure 1A:
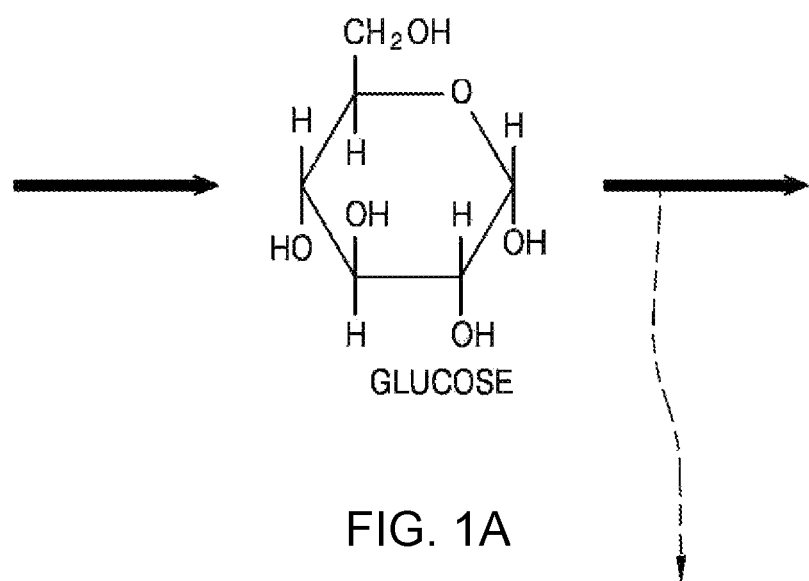
FIGS. 1A and 1B illustrate a principle of a glucose measuring method using an IR, to which the present disclosure is applied.

Reference will now be made in detail to embodiments of the present disclosure, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. A detailed description of related known configurations or functions incorporated herein will be omitted for the sake of clarity and conciseness.

Expressions such as "at least one of," when preceding a list of elements, modify the entire list of elements and do not modify the individual elements of the list.

The terms used herein are general terms that are currently widely used in consideration of functions in the present disclosure but may vary according to such factors as intentions of those of ordinary skill in the art, precedents, and appearances of new technologies. The applicant may arbitrarily select terms in a particular case, and meanings of the terms corresponding to this case will be described in detail in the following description. Therefore, the terms used herein may be defined based on meanings thereof and the overall contents of the embodiments, and not based on names of simple terms.

When a part "comprises" an element in the specification, this may indicate that the part may not exclude and may further include other elements as long as there is no contrary description. The term "unit" used herein refers to a hardware element such as field-programmable gate array (FPGA) or application-specific integrated circuit (ASIC) and performs any role. However, the term "unit" is not limited to software or hardware, and may be constituted to be in a storage medium that may be addressed or may be constituted to play one or more processors. Therefore, for example, the "unit" includes elements, such as software elements, object-oriented elements, class elements, and task elements, processes, functions, attributes, procedures, sub routines, segments of a program code, drivers, firmware, a microcode, a circuit, data, a database (DB), data structures, tables, arrays, and parameters. Functions provided in elements and "units" may be combined as the smaller number of elements and "units" or may be separated as additional elements and "units".

The term "user" used herein refers to a person who desires to measure a blood glucose level of the user by using a glucose measuring apparatus, such as a diabetic.

The term "object" used herein refers to a preset body part of the user for measuring the blood glucose level. For example, the object may be a lip, a tongue, or a finger. The glucose measuring apparatus measures the blood glucose level of the user based on a response of blood or tissue included in the object to an NIR.

Figure 1B:
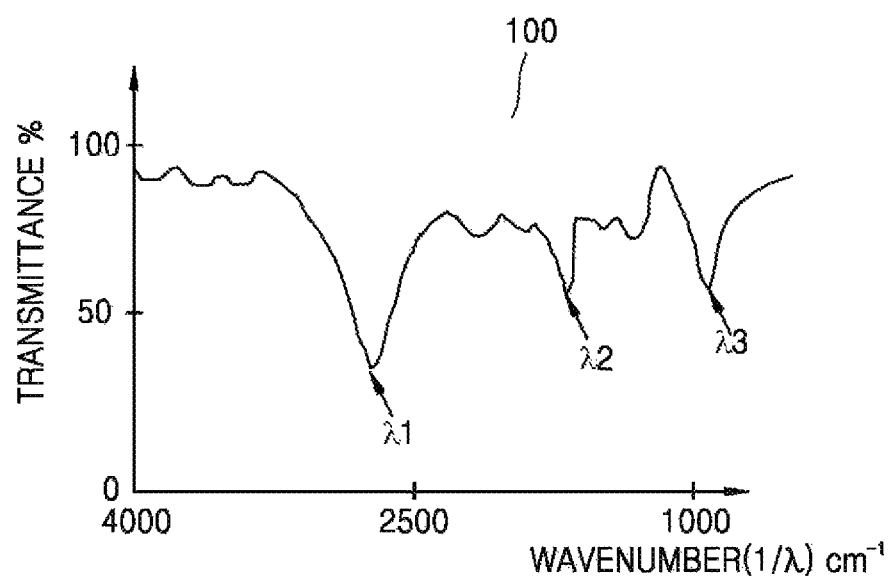

FIGS. 1A and 1B illustrate a principle of a glucose measuring method using an IR, to which the present disclosure is applied.

The glucose measuring method using the IR is based on IR spectroscopy. In detail, molecules may absorb an IR having a particular wavelength according to a combination structure of a molecule, a shape of the molecule, a potential energy surface (PES), masses of atoms, or a vibration coupling. Therefore, on an IR spectrum of a patient, a transmittance or an absorbance of a wavelength absorbed by glucose, which is illustrated in FIG. 1A, may be analyzed to measure a blood glucose level of the patient.

Referring to FIG. 1B, an IR transmittance 100 of glucose with respect to wave numbers is illustrated. For example, glucose may absorb a relatively larger amount of an IR having wavelengths of $\lambda 1$, $\lambda 2$, and $\lambda 3$ than an IR having different wavelengths.

Therefore, on the IR spectrum of the patient, transmittances of the wavelengths $\lambda 1$, $\lambda 2$, and $\lambda 3$ may be analyzed to measure the blood glucose level of the patient. Low transmittances of the wavelengths $\lambda 1$, $\lambda 2$, and $\lambda 3$ indicate a high blood glucose level of the patient.

FIG. 2 illustrates a wavelength of an NIR irradiated by a glucose measuring apparatus according to an embodiment of the present disclosure.

An IR may be classified into an NIR, a mid IR (MIR), and a far IR (FIR) according to a wavelength. For example, a wavelength between about 0.78 μm and about 2.5 microns (μm) may be classified as an NIR, a wavelength between about 2.5 μm and about 25 μm may be classified as a MIR, and a wavelength between about 25 μm and about 250 μm may be classified as a FIR. The above-described sections classifying types of IRs are not limited to the above embodiments and may vary according to classification methods.

A glucose measuring apparatus according to an embodiment of the present disclosure uses an NIR to reduce noise caused by moisture.

When measuring a blood glucose level, a signal-to-noise-ratio (SNR) decreases as a wavelength of an IR increases. As the wavelength of the IR increases, a transmittance to water decreases, and thus noise caused by moisture inside the body increases, such as moisture inside blood and perspiration. Therefore, the glucose measuring apparatus according to an embodiment of the present disclosure uses an NIR having a sufficiently short wavelength among IRs. If an IR other than an NIR is used, most IRs may be absorbed into the moisture inside the body, and thus it is difficult for the glucose measuring apparatus to measure a blood glucose level.

A wavelength 200 of an NIR irradiated by the glucose measuring apparatus according to an embodiment of the present disclosure may be between about 0.8 μm and about 1.8 μm.

When measuring the blood glucose level, as a wavelength of an IR decreases, the distance of the IR from a fingerprint region increases. The fingerprint region refers to a region into which an IR may be absorbed by an individual molecule. A combination region or an overtone region is formed, in which as the wavelength of the IR decreases, energy increases. Thus, the IR is absorbed by different types of molecules, or energies absorbed by different modes are combined with one another. For example, as the wavelength of the IR decreases, there is a high probability that an IR having the same wavelength will be absorbed by glucose and protein. As the wavelength of the IR increases, there is a relatively high probability that an IR having the same wavelength will be absorbed only by glucose. Therefore, an IR having a long wavelength may be used rather than an IR having a short wavelength to precisely measure a blood glucose level. Therefore, the glucose measuring apparatus according to the present embodiment may use a sufficiently long wavelength of an NIR between about 0.8 μm and about 1.8 μm.

FIGS. 3A and 3B illustrate errors occurring due to an external pressure when measuring glucose.

A pressure applied to an object may be a cause of an error occurring when measuring glucose. If the object receives an external pressure, a shape of the object may be changed, and thus a depth of an IR penetrating through the object may change. For example, if a blood vessel receives a pressure, blood diverges from the pressure point. Therefore, a blood volume interacting with irradiated light may be reduced more than before the blood vessel receives the pressure. Therefore, a result of measuring a blood glucose level of the object may change according to the external pressure.

For example, a depth d1 of a blood vessel through which an IR penetrates in an object 310a to which an external pressure is not applied may be deeper than a depth d2 of an IR penetrating through an object 310b to which an external pressure is applied. Therefore, although the objects 310a and 310b are the same, a larger amount of IR may be absorbed into the object 310a to which the external pressure is not applied, and thus a larger amount of glucose may be measured from the object 310b to which the external pressure is applied. As a result, the external pressure may be uniformly maintained to measure an accurate blood glucose level.

Figure 4A:
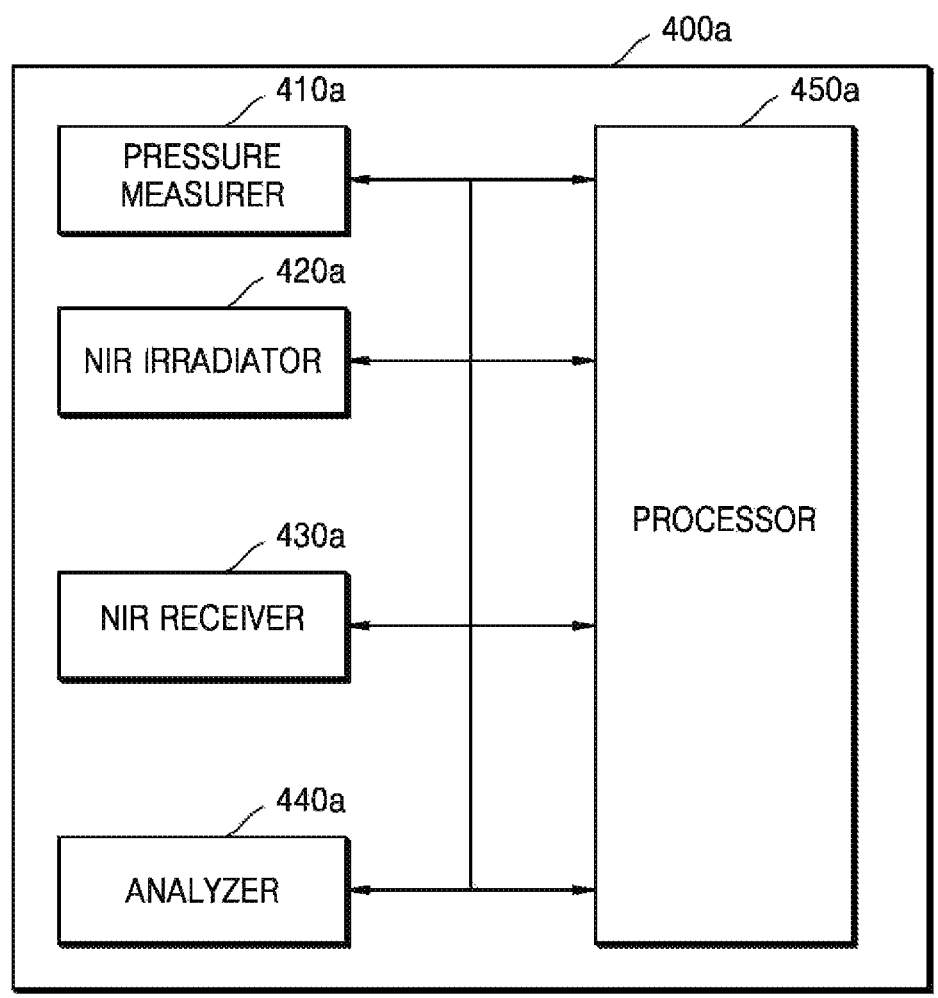
FIGS. 4A and 4B illustrate a structure of a glucose measuring apparatus according to embodiments of the present disclosure.

FIG. 4A illustrates a glucose measuring apparatus 400a according to an embodiment of the present disclosure.

The glucose measuring apparatus 400a according to the present embodiment may directly irradiate an NIR to an object and measure a blood glucose level based on one absorption mode of the NIR reflected from the object, a scattered NIR, and an NIR penetrating through the object.

The glucose measuring apparatus 400a operating in the absorption mode includes a pressure measurer 410a, an NIR irradiator 420a, an NIR receiver 430a, an analyzer 440a, and a processor 450a.

All of the elements illustrated in FIG. 4A are not essential elements of the glucose measuring apparatus 400a. The glucose measuring apparatus 400a may be realized with fewer or more elements than the elements illustrated in FIG. 4A.

The pressure measurer 410a measures a pressure applied to an object.

The pressure measurer 410a measures a pressure generated between the glucose measuring apparatus 400a and the object. A user may cause the glucose measuring apparatus 400a to contact the object to reduce an error occurring due to a noncontact of a light source with a skin surface so as to measure an accurate blood glucose level. Therefore, the pressure is generated between the glucose measuring apparatus 400a and the object.

If a preset pressure measured by the pressure measurer 410a is greater than or equal to a preset value, the NIR irradiator 420a irradiates an NIR to the object.

As described above with reference to FIGS. 3A and 3B, if the pressure generated between the glucose measuring apparatus 400a and the object changes whenever an IR is irradiated, a shape of the object may be changed, causing a change in a blood volume, which interacts with the IR when the IR penetrates through the object.

Therefore, the NIR irradiator 420a may control a time when an NIR is irradiated and thus reduce errors occurring when measuring glucose based on the pressure measured by the pressure measurer 410a. For example, if the pressure measured by the pressure measurer 410a exceeds a preset value when the user causes the glucose measuring apparatus 400a to contact the object, the NIR irradiator 420a may irradiate an NIR to the object.

The NIR receiver 430a may receive at least one of an NIR reflected from the object, a scattered NIR, and an NIR penetrating through the object.

The analyzer 440a measures a blood glucose level based on the NIR received by the NIR receiver 430a.

The analyzer 440a may measure the blood glucose level based on an IR spectroscopy as described above with reference to FIG. 1. In other words, the analyzer 440a may analyze an absorption depending on a wavelength of the received NIR to measure the blood glucose level and analyze a type of glucose included in the object.

The processor 450a controls an overall operation of the glucose measuring apparatus 400a. For example, the processor 450a may execute programs stored in a memory to control overall operations of the pressure measurer 410a, the NIR irradiator 420a, the NIR receiver 430a, and the analyzer 440a.

Figure 4B:
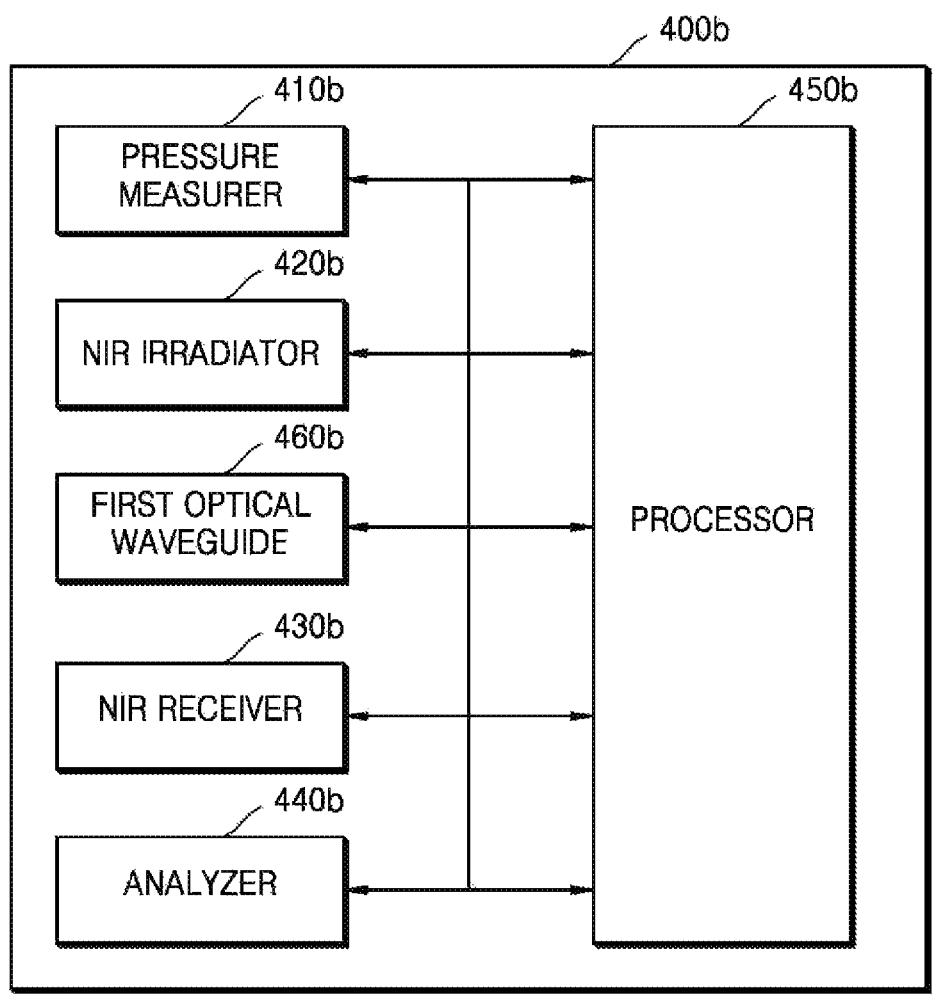

FIG. 4B illustrates a glucose measuring apparatus 400b according to another embodiment of the present disclosure.

The glucose measuring apparatus 400b irradiates an NIR to an object and measures a blood glucose level based on an attenuated total reflection (ATR)-NIR, which will be referred to hereinafter as an ATR mode for convenience of description.

The ATR-NIR refers to a technology that may analyze a material by using a phenomenon in which when an NIR is completely reflected in an optical waveguide, the NIR leaves a core and then reenters the core of the optical waveguide. When the NIR is propagated in the optical waveguide through a total reflection, an evanescent wave may be generated. The evanescent wave refers to an NIR, a part of which is propagated from a boundary surface of the optical waveguide to an outside area when being completely reflected in the optical waveguide. Therefore, the evanescent wave, a part of which is absorbed into the object, may be excluded from the ATR-NIR in comparison with an initially irradiated NIR. If the evanescent wave is absorbed into the object, the glucose measuring apparatus 400b may measure a blood glucose level through a spectrum of the ATR-NIR.

The glucose measuring apparatus 400b operating in the ATR mode includes a pressure measurer 410b, an NIR irradiator 420b, an NIR receiver 430b, an analyzer 440b, a first optical waveguide 460b, and a processor 450b.

All of elements illustrated in FIG. 4B are not essential elements of the glucose measuring apparatus 400b. The glucose measuring apparatus 400b may be realized by fewer or more elements than the elements illustrated in FIG. 4B.

The pressure measurer 410 measures a pressure applied to the object.

The pressure measurer 410b measures a pressure generated between the glucose measuring apparatus 400b and the object. A user may cause the glucose measuring apparatus 400b contact the object to enable the evanescent wave to penetrate through the object so as to measure a precise blood glucose level. Therefore, a pressure is generated between the glucose measuring apparatus 400b and the object.

The glucose measuring apparatus 400b includes the first optical waveguide 460b close to the object, to enable the evanescent wave to penetrate through the object.

If the pressure measured by the pressure measurer 410b is greater than or equal to a preset value, the NIR irradiator 420b irradiates an NIR to the first optical waveguide 460b.

As described above with reference to FIGS. 3A and 3B, if the pressure generated between the glucose measuring apparatus 400b and the object is changed whenever an IR is irradiated, a shape of the object is changed, causing a change in a depth of the object through which the IR penetrating and a blood volume which interacts with the IR.

Therefore, the NIR irradiator 420b may control a time when the NIR is irradiated and reduce errors occurring when measuring glucose, based on the pressure measured by the pressure measurer 410b. For example, if the pressure measured by the pressure measurer 410b exceeds the preset value when the user causes the glucose measuring apparatus 400b to contact the object, the NIR irradiator 420b may irradiate the NIR to the first optical waveguide 460b.

The NIR receiver 430b receives an ATR-NIR from the first optical waveguide 460b.

The analyzer 440b measures a blood glucose level based on the ATR-NIR received by the NIR receiver 430b.

As described above with reference to FIG. 1, the analyzer 440b may measure the blood glucose level based on an IR spectroscopy. In other words, the analyzer 440b may analyze an absorption depending on a wavelength of the ATR-NIR to measure the blood glucose level and analyze a type of glucose included in the object.

The processor 450b controls an overall operation of the glucose measuring apparatus 400b. For example, the processor 450b may execute programs stored in a memory to control overall operations of the pressure measurer 410b, the NIR irradiator 420b, the NIR receiver 430b, and the analyzer 440b.

The glucose measuring apparatuses 400a and 400b may measure a blood glucose level of an object a plurality of times to calculate an average value of the blood glucose levels.

The glucose measuring apparatuses 400a and 400b may measure a blood glucose level by using an IR for a very short time period. Therefore, if a pressure measured by the pressure measurers 410a and 410b is greater than or equal to a preset value, the NIR irradiators 420a and 420b may irradiate an NIR a plurality of times. In this case, the analyzers 440a and 440b may measure blood glucose levels respectively with respect to IRs that are irradiated a plurality of times and calculate an average value of a plurality of blood glucose levels. The glucose measuring apparatuses 400a and 400b may measure an average value to further accurately measure a blood glucose level.

Figure 5:
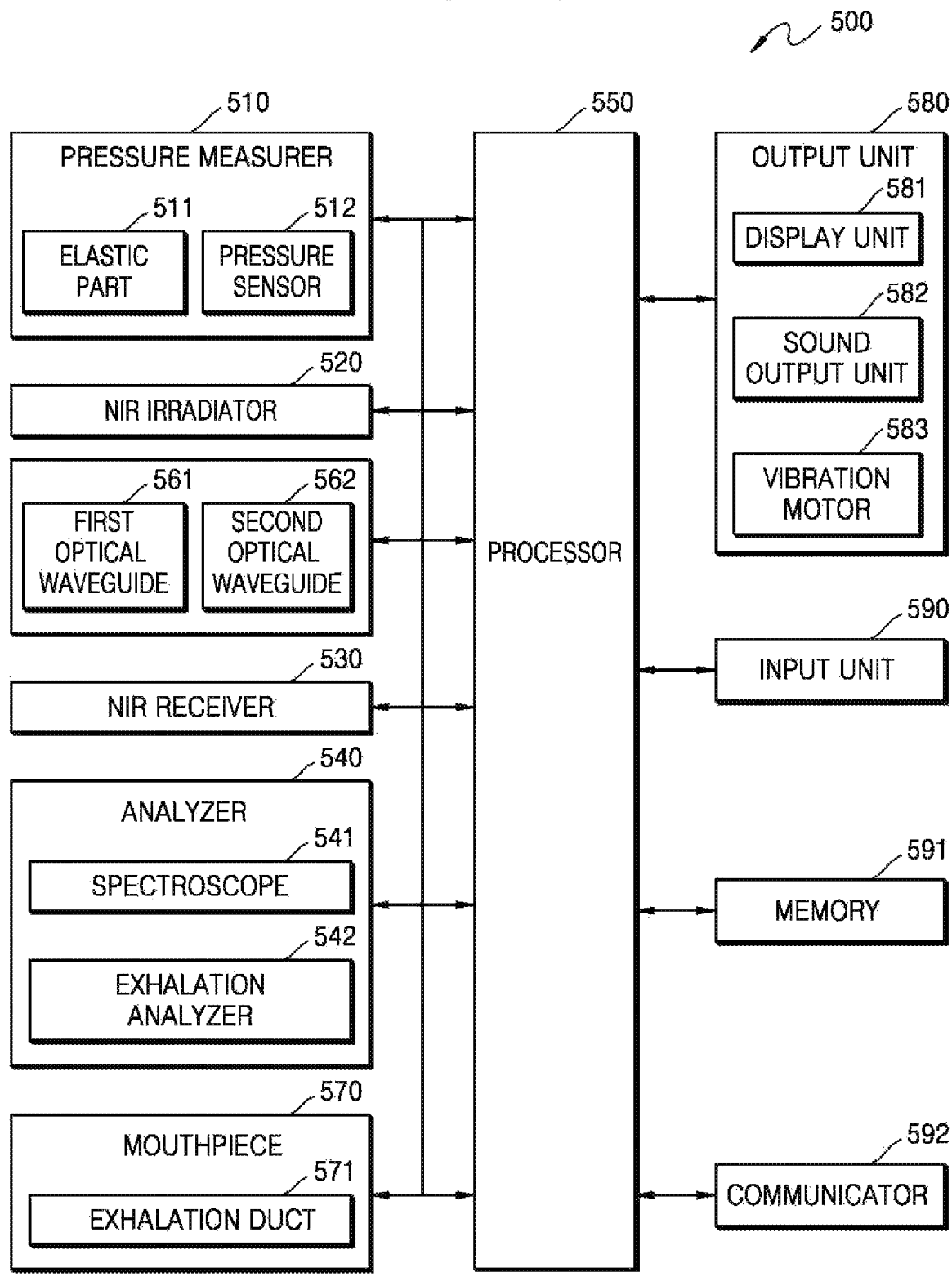
FIG. 5 illustrates a structure of a glucose measuring apparatus according to another embodiment of the present disclosure.

FIG. 5 illustrates a structure of a glucose measuring apparatus 500 according to another embodiment of the present disclosure.

The glucose measuring apparatus 500 according to the present embodiment may select one of an absorption mode and an ATR mode to measure a blood glucose level. Alternatively, the glucose measuring apparatus 500 may measure the blood glucose level based on both of the absorption mode and the ATR mode.

The glucose measuring apparatus 500 of FIG. 5 may include at least one of the glucose measuring apparatus 400a of FIG. 4A and the glucose measuring apparatus 400b of FIG. 4B. A pressure measurer 510, an NIR irradiator 520, an NIR receiver 530, an analyzer 540, and a processor 550 of the glucose measuring apparatus 500 of FIG. 5 may respectively correspond to the pressure measurer 410a, the NIR irradiator 420a, the NIR receiver 430a, the analyzer 440a, and the processor 450a of FIG. 4A, and the pressure measurer 510, the NIR irradiator 520, the NIR receiver 530, the analyzer 540, the processor 550, and a first optical waveguide 561 may respectively correspond to the pressure measurer 410b, the NIR irradiator 420b, the NIR receiver 430b, the analyzer 440b, the processor 450b, and the first optical waveguide 460b of FIG. 4B. Therefore, the same descriptions of elements of FIG. 5 as those of the elements of FIGS. 4A and 4B are omitted.

In comparison with the glucose measuring apparatuses 400a and 400b of FIGS. 4A and 4B, the glucose measuring apparatus 500 of FIG. 5 may further include at least one of a second optical waveguide 562, a mouthpiece 570, an output unit 580, an input unit 590, a memory 591, and a communicator 592.

The pressure measurer 510 may include at least one of an elastic part 511 and a pressure sensor 512.

The elastic part 511 may endure a pressure applied to the object. When the user causes the glucose measuring apparatus 500 to contact the object, a pressure generated between the glucose measuring apparatus 500 and the object may be applied by the elastic part 511. The pressure measurer 510 may measure the pressure the elastic part 511 receives. For example, if the pressure the elastic part 511 receives is greater than or equal to a preset value, the pressure measurer 510 may activate a preset switch. The glucose measuring apparatus 500 including the elastic part 511 will be described in more detail later with reference to FIGS. 6A through 6C.

The pressure measurer 510 may measure a pressure applied to the object through the pressure sensor 512. When the user causes the glucose measuring apparatus 500 to contact the object, the pressure sensor 512 may measure the pressure generated between the glucose measuring apparatus 500 and the object. The glucose measuring apparatus 500 including the pressure sensor 512 will be described in more detail later with reference to FIGS. 7A through 7C.

The glucose measuring apparatus 500 according to the present embodiment may have the same shape as a shape of the mouthpiece 570 that the object is close to or contacts. Since an NIR that is reflected from a human body and has a long wavelength includes information close to a skin surface, a body part that is close to the skin and has many blood vessels may be an efficient object of the glucose measuring apparatus 500. For example, a lip or a tongue may be the efficient object of the glucose measuring apparatus 500.

Therefore, the glucose measuring apparatus 500 may have the same shape as a shape of the mouthpiece 570 so as to irradiate an NIR to a lip or a tongue. The mouthpiece 570 may be a housing of the glucose measuring apparatus 500 that the user may hold in place between the lips and gums. The first optical waveguide 561 may be positioned on the mouthpiece 570 so as to enable the evanescent wave to be effectively absorbed into the object.

The glucose measuring apparatus 500 according to the present embodiment may measure a blood glucose level based on an exhalation of the user rather than an IR. The mouthpiece 570 may include an exhalation duct 571 through which the exhalation of the user passes. The analyzer 540 may analyze, for example, a density of acetone, methyl nitrate, toluene, isoprene, carbon monoxide, 2-pentanone, acetonitrile, or acrylonitrile included in the exhalation of the user to measure a blood glucose level. The analyzer 540 may also be classified as a spectroscope 541 and an exhalation analyzer 540 to analyze an NIR and an exhalation.

The output unit 580 may output an audio signal, a video signal, or a vibration signal and include a display unit 581, a sound output unit 582, and a vibration motor 583.

The display unit 581 displays and outputs information processed by the glucose measuring apparatus 500, such as a blood glucose level measured by the analyzer 540. The display unit 581 may also display a user interface (UI) such as for selecting a virtual image or for setting an operation of the virtual image.

The display unit 581 may include at least one of a liquid crystal display (LCD), a thin film transistor-LCD (TFT-LCD), an organic light-emitting diode (OLED), a flexible display, a 3-dimensional (3D) display, and an electrophoretic display.

The sound output unit 582 outputs audio data that is received from the communicator 592 or stored in the memory 591. The sound output unit 582 also outputs a sound signal related to a function such as a call signal reception sound, a message reception sound or an alarm performed by the glucose measuring apparatus 500. The sound output unit 582 may include a speaker or a buzzer, for example.

A vibration motor 583 outputs a vibration signal corresponding to an output of audio data or video data, such as a call signal reception sound or a message reception sound. The vibrator motor 583 may also output the vibration signal if a touch is input on a touch screen.

The input unit 590 generates and outputs a UI screen for receiving a preset command or data from the user, and receives the preset command or data from the user through the UI screen. The UI screen output from the input unit 590 is output to the display unit 581. However, the display unit 581 may display the UI screen. The user may see the UI screen displayed through the display unit 581 to recognize preset information and input a preset command or data.

For example, the input unit 590 may include a mouse, a keyboard, and an input unit including hard keys for inputting preset data, any of which the user may manipulate to input preset data or command.

The input unit 590 may be formed as a touch pad that is combined with a display panel included in the display unit 581, and outputs the UI screen onto the display panel. If a preset command is input through the UI screen, the touch pad may sense the preset command to recognize the preset command input by the user.

If the input unit 590 is formed as the touch pad, and the user touches a preset point of the UI screen, the input unit 590 senses the touched preset point and may transmit sensed information to the processor 550 recognize a request or a command of the user corresponding to a menu displayed at the sensed point and perform the recognized request or command.

The memory 591 may store various types of data for measuring a blood glucose level and a program for testing blood, for example. The memory 591 may include a storage medium of at least one type of a flash memory type, a hard disc type, a multimedia card micro type, a card type memory such as a secure digital (SD) memory or an XD memory, a random access memory (RAM), a static RAM (SRAM), a read only memory (ROM), a programmable ROM (PROM), a magnetic memory, a magnetic disk, and an optical disk. The memory 591 may store a process, a progress process, and a test result acquired when measuring a blood glucose level.

The communicator 592 may include one or more elements that enable data communication to be performed between the glucose measuring apparatus 500 and another device or between the glucose measuring apparatus 500 and a server. For example, the communicator 592 may transmit a blood glucose level measured by the glucose measuring apparatus 500 to a server of a hospital.

Figure 6A:
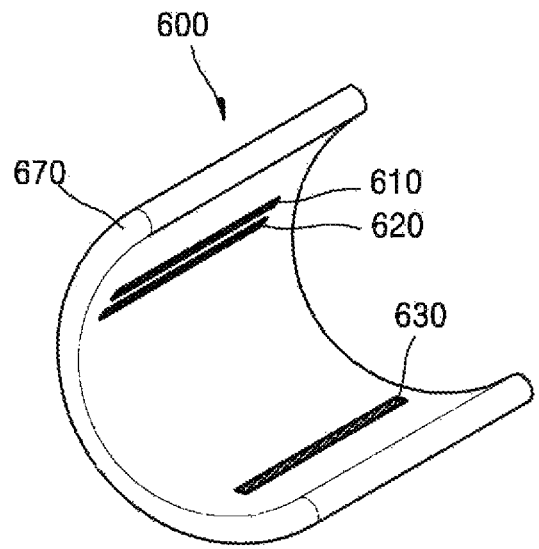
FIGS. 6A, 6B and 6C illustrate an operation of a glucose measuring apparatus that irradiates a NIR to an object, an according to embodiment of the present disclosure.
Figure 6B:
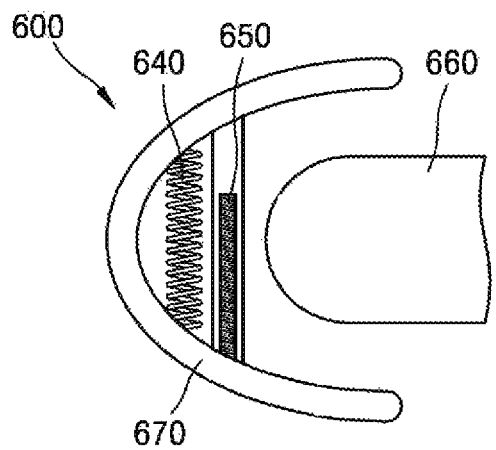
Figure 6C:
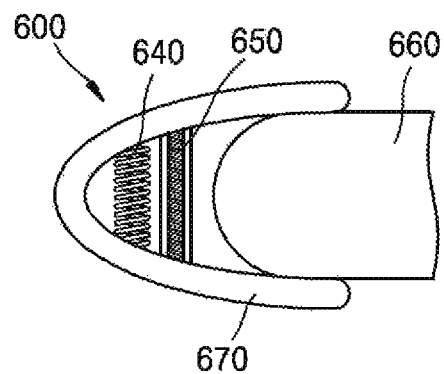

FIGS. 6A, 6B and 6C illustrate an operation of a glucose measuring apparatus 600 that irradiates an NIR to an object, according to an embodiment of the present disclosure.

FIG. 6A illustrates the portable glucose measuring apparatus 600 according to an embodiment of the present disclosure. A diabetic may periodically and continuously measure a blood glucose level, making it desirable for the glucose measuring apparatus 600 to be sufficiently small and highly portable. In addition, the glucose measuring apparatus 600 may be combined with a portable device such as a smartphone or a wearable device, which will be described in more detail later with reference to FIG. 9.

The glucose measuring apparatus 600 may include pressure measurers 640 and 650, an NIR irradiator 610, NIR receivers 620 and 630, and an analyzer.

If a pressure measured by the pressure measurers 640 and 650 is greater than or equal to a preset value, the NIR irradiator 610 irradiates an NIR having a plurality of wavelengths to an object. A wavelength of an NIR irradiated by the NIR irradiator 610 may be between about 0.8 µm and about 1.8 µm. The glucose measuring apparatus 600 may use an NIR having a wavelength between about 0.8 µm and 1.8 µm to reduce noise made by body moisture in a fingerprint region so as to efficiently measure a blood glucose level.

The NIR receivers 620 and 630 receive at least one of an NIR reflected from the object, a scattered NIR, and an NIR penetrating through the object. For example, a part of or the entire NIR receiver 620 may be positioned to be parallel with the NIR irradiator 610 on the glucose measuring apparatus 600 so as to receive an NIR reflected or scattered from the object. As another example, a part of or the entire NIR receiver 630 may be positioned to face the NIR irradiator 610 on the glucose measuring apparatus 600 so as to receive an NIR penetrating the object.

The analyzer may analyze a blood glucose level based on the NIR received by the NIR receivers 620 and 630. On a spectrum of a received NIR, the analyzer measures a high blood glucose level as a transmittance of a wavelength absorbed by glucose is low.

The glucose measuring apparatus 600 may have virtually the same shape as a shape of a mouthpiece 670 to which the object, i.e., a lower lip 660, is close. For example, a housing of the glucose measuring apparatus 600 may have virtually the same shape as the shape of the mouthpiece 670. The mouthpiece 670 may have generally an arch shape so as to enable the lower lip 660 of the user to be inserted into the mouthpiece 670.

FIG. 6B illustrates the glucose measuring apparatus 600 where the lip 660 does not contact the mouthpiece 670. FIG. 6C illustrates the glucose measuring apparatus 600 where the lip 660 contacts the mouthpiece 670.

The pressure measurers 640 and 650 measure a pressure applied to the object. For example, the pressure measurers 640 and 650 may include the elastic part 640 that receive the pressure applied to the object. As the user causes the glucose measuring apparatus 600 to contact the object, a pressure generated between the glucose measuring apparatus 600 and the object may be applied to the elastic part 640. For example, if the user makes the lip 660 contact the mouthpiece 670 and presses the mouthpiece 670 with a hand, a pressure may be applied to the elastic part 640.

The pressure measurers 640 and 650 may measure the pressure the elastic part 640 receive. For example, the pressure measurers 640 and 650 includes a switch 650 that is turned on if the pressure the elastic part 640 receives is greater than or equal to a preset value. As the pressure applied to the elastic part 640 gradually increases, the elastic part 640 may gradually shrink, and thus the switch 650 may be connected.

The NIR irradiator 610 may irradiate an NIR to a lip if the switch 650 is turned on.

The glucose measuring apparatus 600 may control the amount of time to irradiate an NIR according to a pressure applied to the object, to reduce errors occurring due to a pressure that may be generated when measuring a blood glucose level.

Figure 7A:
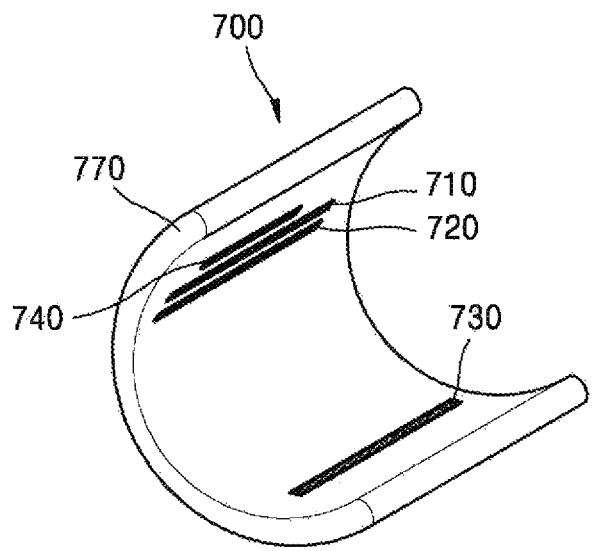
FIGS. 7A, 7B and 7C illustrate an operation of a glucose measuring apparatus that irradiates an NIR to an object, according to another embodiment of the present disclosure.
Figure 7B:
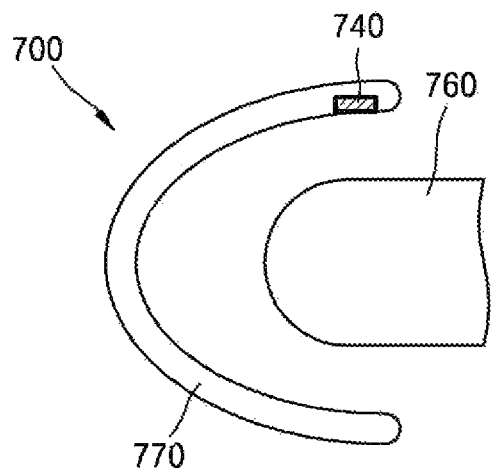
Figure 7C:
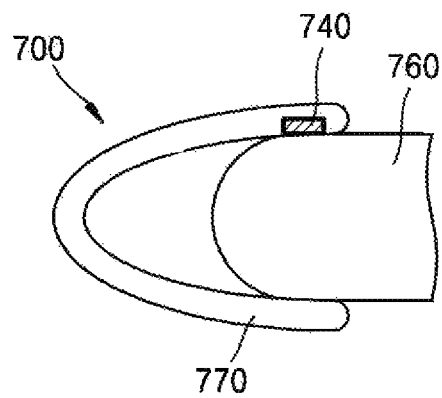

FIGS. 7A, 7B and 7C illustrate an operation of a glucose measuring apparatus 700 that irradiates an NIR to an object, according to another embodiment of the present disclosure.

Specifically, FIG. 7A illustrates the portable glucose measuring apparatus 700, FIG. 7B illustrates the glucose measuring apparatus 700 where a lip 760 does not contact a mouthpiece 770, and FIG. 7C illustrates the glucose measuring apparatus 700 where the lip 760 contacts the mouthpiece 770.

Comparing FIG. 7 with FIG. 6, a pressure measurer of FIG. 7 may include a pressure sensor 740 instead of the elastic part 640. However, elements of the glucose measuring apparatus 700 of FIG. 7 may respectively correspond to elements of the glucose measuring apparatus 600 of FIG. 6. That is, an NIR irradiator 710, NIR receivers 720 and 730, an analyzer, and a mouthpiece 770 may respectively correspond to the NIR irradiator 610, the NIR receivers 620 and 630, the analyzer, and the mouthpiece 670. Therefore, the same descriptions of the elements of FIG. 7 as those of the elements of FIG. 6 are omitted, for conciseness.

The pressure sensor 740 may measure a pressure generated between the glucose measuring apparatus 700 and the object. As a user causes the glucose measuring apparatus 700 to contact the object, the pressure sensor 740 may measure the pressure generated between the glucose measuring apparatus 700 and the object. For example, the pressure sensor 740 may be positioned on the mouthpiece 770. If the user causes the lip 760 to contact the mouthpiece 770 and applies pressure to the mouthpiece 770 with a hand, the pressure sensor 740 may measure a pressure generated between the mouthpiece 770 and the lip 760.

If the pressure measured by the pressure sensor 740 is greater than or equal to a preset value, the NIR irradiator 710 may also irradiate an NIR to the object.

Figure 8A:
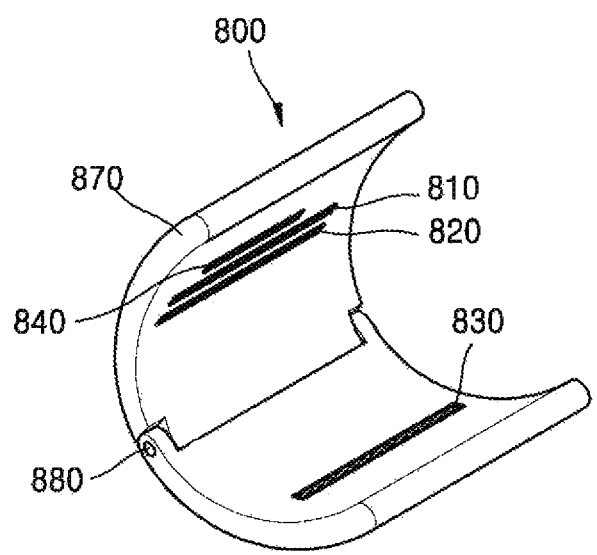
FIGS. 8A. 8B and 8C illustrate an operation of a glucose measuring apparatus that irradiates an NIR to an object, according to another embodiment of the present disclosure.
Figure 8B:
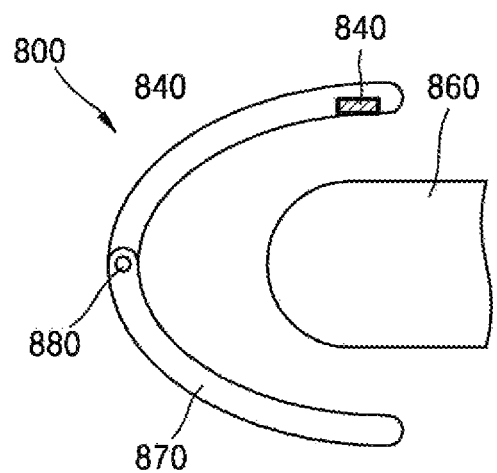
Figure 8C:
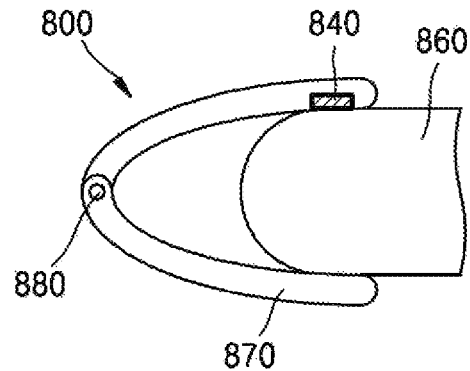

FIG. 8A illustrates a portable glucose measuring apparatus 800, FIG. 8B illustrates the glucose measuring apparatus 800 where a lip 860 does not contact a mouthpiece 870, and FIG. 8C illustrates the glucose measuring apparatus 800 where the lip 860 contacts the mouthpiece 870, according to another embodiment of the present disclosure.

Comparing FIG. 8 with FIG. 7, the glucose measuring apparatus 800 of FIG. 8 may further include a pressurizer 880. Elements of the glucose measuring apparatus 800 except the pressurizer 880 may respectively correspond to the elements of the glucose measuring apparatus 700 of FIG. 7. That is, an NIR irradiator 810, NIR receivers 820 and 830, an analyzer, the mouthpiece 870, and a pressure sensor 840 of FIG. 8 may respectively correspond to the NIR irradiator 710, the NIR receivers 720 and 730, the analyzer, the mouthpiece 770, and the pressure sensor 740. Therefore, the same descriptions of the elements of FIG. 8 as those of the elements of FIG. 7 are omitted for conciseness.

The pressurizer 880 may apply a pressure to an object. For example, the pressurizer 880 may include a hinge positioned on the mouthpiece 870 to apply the pressure to the object. Therefore, differently from the glucose measuring apparatus 700 of FIG. 7, a user may not apply a pressure to the glucose measuring apparatus 800 of FIG. 8.

The pressure sensor 840 measures a pressure applied to the object by the pressurizer 880. If the pressure measured by the pressure sensor 840 is greater than or equal to a preset value, the NIR irradiator 810 may irradiate an NIR to the object.

The glucose measuring apparatus 800 may control the amount of time to irradiate an NIR according to the pressure applied to the object and the pressure applied to the object to reduce errors that may occur due to the pressure when measuring a blood glucose level.

Figure 9A:
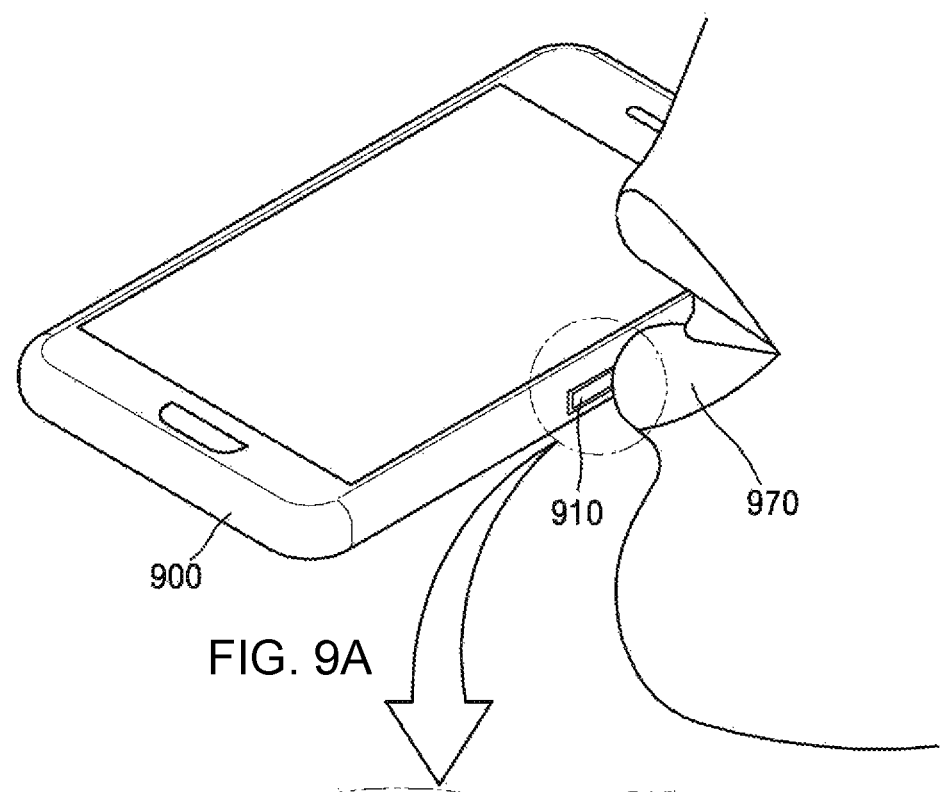
FIGS. 9A and 9B illustrate a glucose measuring apparatus that is combined with a portable device according to an embodiment of the present disclosure.
Figure 9B:
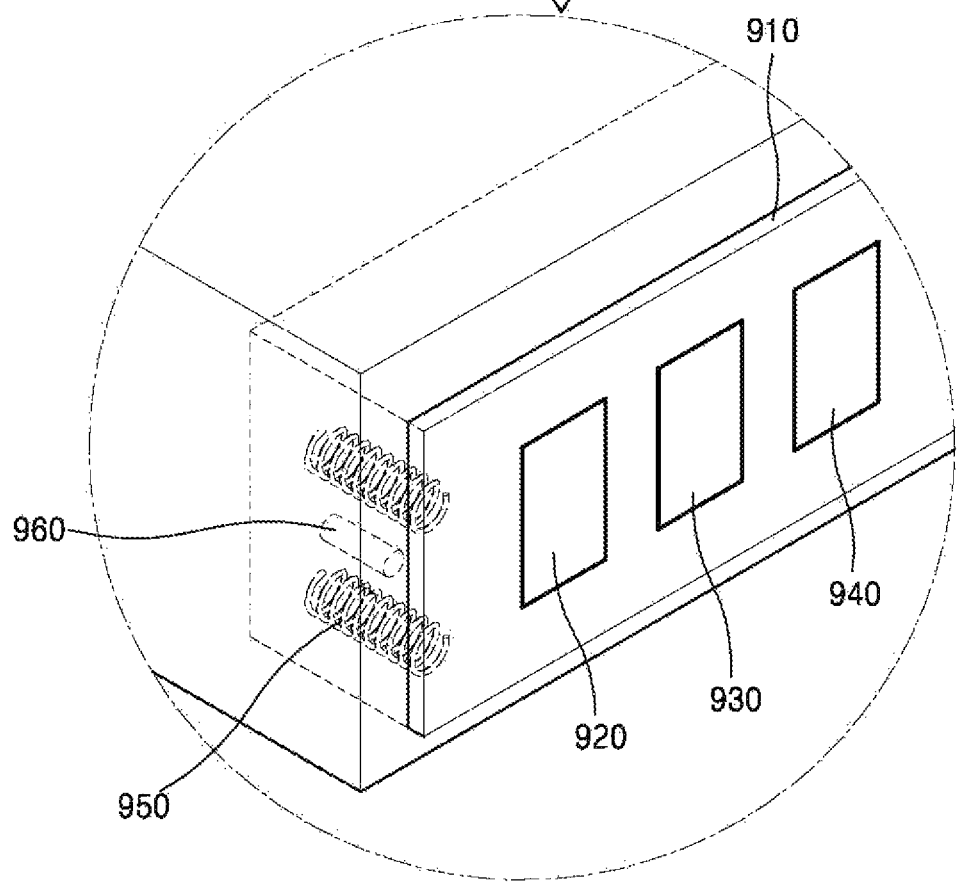

FIGS. 9A and 9B illustrate a glucose measuring apparatus 910 that is combined with a portable device 900, according to an embodiment of the present disclosure. Specifically, FIG. 9A illustrates an operation of the glucose measuring apparatus 910 that is combined with the portable device 900 and measures a blood glucose level, and FIG. 9B illustrates an enlarged view of the glucose measuring apparatus 910 that is combined with the portable device 900.

The glucose measuring apparatus 910 may be combined with the portable device 900 such as a smartphone or a wearable device, on one side of the portable device 900.

In FIG. 9B, the glucose measuring apparatus 910 may further include pressure measurers 950 and 960, NIR irradiators 920 and 940, an NIR receiver 930, and an analyzer. The pressure measurers 950 and 960 may include an elastic part 950 that receive a pressure applied to an object and a switch 960 that is turned on if the pressure applied to the object is greater than or equal to a preset value. As a pressure applied to the elastic part 950 increases, the elastic part 950 shrinks to enable the switch 960 to be connected.

For example, if the user causes a lip 970 to contact the glucose measuring apparatus 910, a pressure generated between the lip 970 and the glucose measuring apparatus 910 is applied to the elastic part 950. Due to the shrinkage of the elastic part 950, the switch 960 may be connected, and the NIR irradiators 920 and 940 may irradiate an NIR to the lip 970.

The NIR irradiators 920 and 940 may be realized to irradiate only an NIR having a particular wavelength so as to compress the glucose measuring apparatus 910. The NIR irradiators 920 and 940 may be realized to irradiate preset wavelengths for efficiently measuring a blood glucose level. For example, the NIR irradiators 920 and 940 may include the first NIR irradiator 920 that irradiates an NIR having a relatively short wavelength of about 0.8 μm and the second NIR irradiator 940 that irradiates an NIR having a relatively long wavelength of about 1.8 μm.

The NIR irradiators 920 and 940 may be generally symmetrical to each other based on the NIR receiver 930. For example, a plurality of NIR irradiators 920 and 940 may be positioned on a circular arc from the NIR receiver 930.

The NIR receiver 930 receives at least one of an NIR reflected from the object, a scattered NIR, and an NIR penetrating through the object, and the analyzer analyzes a blood glucose level based on the received NIR.

Figure 10A:
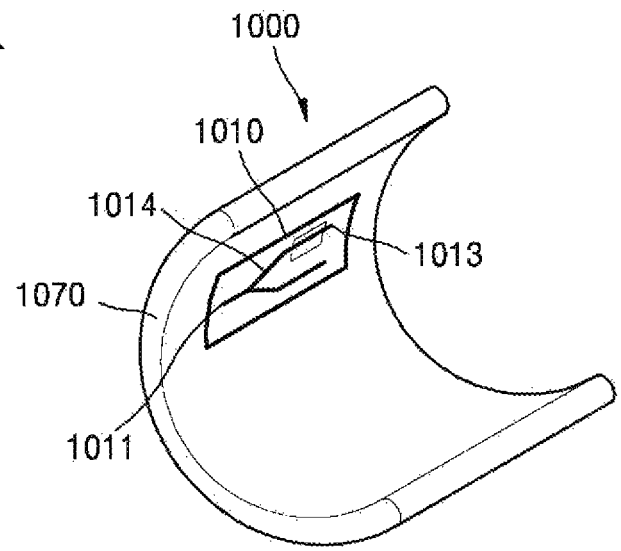
FIGS. 10A. 10B and 10C illustrate an operation of a glucose measuring apparatus using an attenuated total reflection (ATR)-NIR, according to an embodiment of the present disclosure.
Figure 10B:
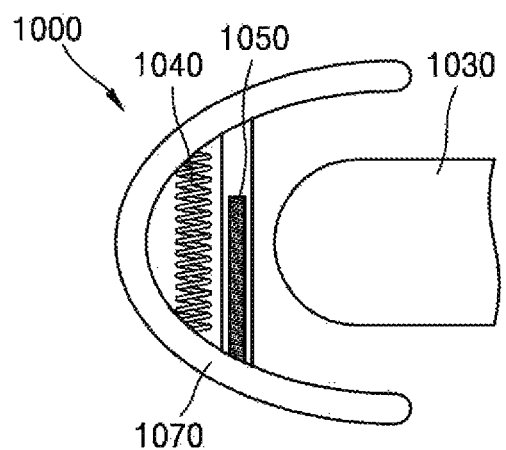
Figure 10C:
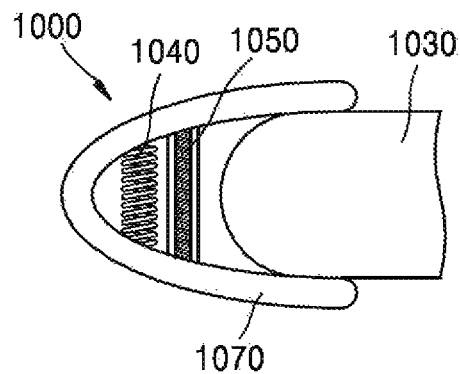

FIGS. 10A, 10B and 10C illustrate an operation of a glucose measuring apparatus 1000 using an ATR-NIR, according to an embodiment of the present disclosure.

As described above with reference to FIGS. 6 through 9, the glucose measuring apparatus 1000 according to the present embodiment may directly irradiate an NIR to an object to measure a blood glucose level based on one of an NIR reflected from the object, a scattered NIR, and an NIR penetrating through the object.

The glucose measuring apparatus 1000 may also irradiate an NIR to an optical waveguide to measure a blood glucose level based on an ATR-NIR.

The glucose measuring apparatus 1000 may use an absorption mode and an ATR mode together. The glucose measuring apparatus 1000 may also selectively use the absorption mode and the ATR mode. The absorption mode has been described above with reference to FIGS. 6 through 9, and thus the glucose measuring apparatus 1000 using the ATR mode will now be described.

FIG. 10A illustrates the glucose measuring apparatus 1000 according to another embodiment of the present disclosure.

The glucose measuring apparatus 1000 may include pressure measurers 1040 and 1050, a film 1010 including a first optical waveguide 1014, a mouthpiece 1070, an NIR irradiator 1014, an NIR receiver 1013, and an analyzer.

The first optical waveguide 1014 and the film 1010 including the first optical waveguide 1014 will be described in detail later with reference to FIGS. 11A, 11B and 11C.

If a pressure measured by the pressure measurers 1040 and 1050 is greater than or equal to a preset value, the NIR irradiator 1014 irradiates an NIR having a plurality of wavelengths to the first optical waveguide 1014, such as between about 0.8 μm and about 1.8 μm. The glucose measuring apparatus 1000 may reduce noise made by body moisture in a fingerprint region by using an NIR having a wavelength between about 0.8 μm and about 1.8 μm to efficiently measure a blood glucose level.

The NIR receiver 1013 receives an ATR-NIR from the first optical waveguide 1014. An NIR irradiated from the NIR irradiator 1014 is propagated through the first optical waveguide 1014. Therefore, an evanescent wave is generated, and thus a portion of the NIR is absorbed into the object. Therefore, the NIR receiver 1013 may receive an ATR-NIR from the first optical waveguide 1014.

The analyzer may analyze a blood glucose level based on the ATR-NIR received by the NIR receiver 1013. In detail, on a spectrum of the received ATR-NIR, the analyzer measures a high blood glucose level as a transmittance of an NIR having a wavelength absorbed by glucose is low.

The glucose measuring apparatus 1000 may have virtually the same shape as a shape of the mouthpiece 1070 that a lip 1030 is close to or contacts. For example, a housing of the glucose measuring apparatus 1000 may have virtually the same shape of the shape of the mouthpiece 1070. The mouthpiece 1070 may have generally an arch structure so as to easily receive insertion of the lower lip 1030.

FIG. 10B illustrates the glucose measuring apparatus 1000 where the lip 1030 does not contact the mouthpiece 1070. FIG. 10C illustrates the glucose measuring apparatus 1000 where the lip 1030 contacts the mouthpiece 1070.

The pressure measurers 1040 and 1050 of FIGS. 10A, 10B and 10C may correspond to the pressure measurers 1040 and 1050 of FIG. 6. The elastic part 1040 that receives a pressure applied to the object and the switch 1050 that is turned on if the pressure received by the elastic part 1040 is greater than or equal to or preset value may respectively correspond to the elastic part 1040 and the switch 1050 of FIGS. 6A, 6B and 6C. Therefore, the same descriptions of elements of FIGS. 10A, 10B and 10C as those of the elements of FIGS. 6A, 6B and 6C are omitted for conciseness.

The pressure measurers 1040 and 1050 may include a pressure sensor. Instead of the elastic part 1040 and the switch 1050, the pressure sensor may be used to measure a pressure generated between the mouthpiece 1070 and the object.

Figure 11A:
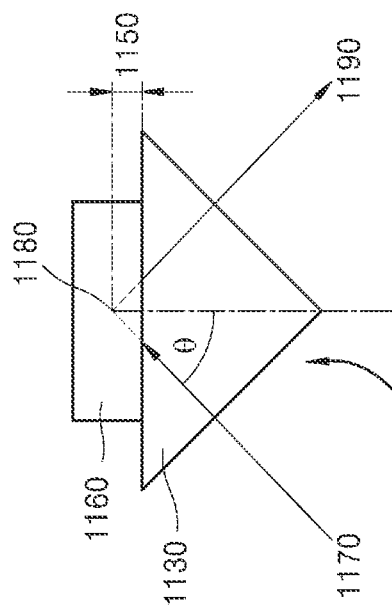
FIGS. 11A, 11B and 11C illustrate a structure of the glucose measuring apparatus of FIGS. 10A, 10B and 10C.
Figure 11B:
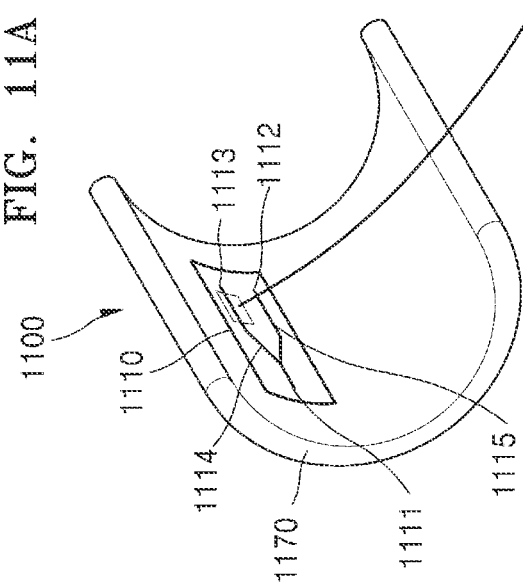
Figure 11C:
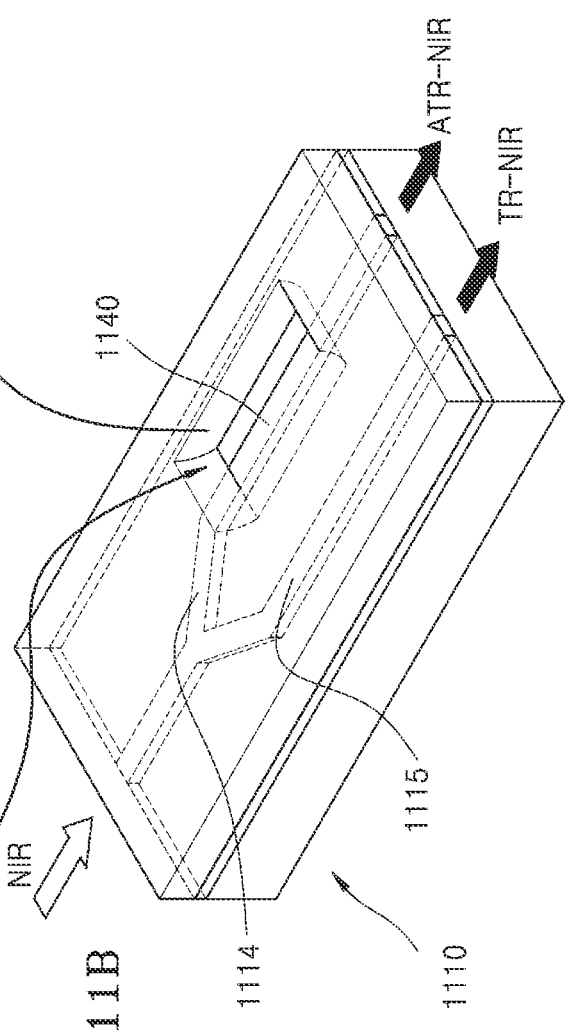

FIGS. 11A, 11B and 11C illustrate a structure of a glucose measuring apparatus 1100 as shown in FIGS. 10A, 10B and 10C, according to an embodiment of the present disclosure.

The glucose measuring apparatus 1100 of FIG. 11A may correspond to the glucose measuring apparatus 1000 of FIG. 10A. Therefore, the same descriptions of the glucose measuring apparatus 1100 as those of the glucose measuring apparatus 1000 of FIGS. 10A, 10B and 10C are omitted for conciseness.

FIG. 11B illustrates a film 1110 including a first optical waveguide 1114. The film 1110 refers to an independent module that is combined with and separated from the glucose measuring apparatus 1100.

The first optical waveguide 1114 is close to an object so as to enable an evanescent wave to be absorbed into the object. For example, the first optical waveguide 1114 may be positioned on a mouthpiece 1170.

The first optical waveguide 1114 may include polymer such as at least one of polymethyl methacrylate (PMMA), poly styrene (PS), and polycarbonate (PC).

Since a depth of the evanescent wave that penetrates through the object is very shallow, coupling between the object and the first optical waveguide 1114 is vital to precisely measure a blood glucose level. In other words, when the object is direct to the first optical waveguide 1114 without a gap, a blood glucose level may be precisely measured.

In general, an IR spectroscopy using an ATR uses a crystal optical waveguide formed of Zinc Selenide (ZnSe) or Germanium (Ge). The crystal optical waveguide having no elasticity may be inefficiently coupled to the object. Although the crystal optical waveguide receives a pressure from the object, a shape of the crystal optical waveguide is not changed, making it difficult for the crystal optical waveguide to be close to the object without a gap. Therefore, if the crystal optical waveguide is used, it is difficult for the evanescent wave to be absorbed into the object, and an error may occur when measuring a blood glucose level.

The first optical waveguide 1114 of the glucose measuring apparatus 1100 according to the present embodiment may include a polymer to be efficiently coupled to the object, since the first optical waveguide 1114 may become flexible and, therefore, is close to the object without a gap. For example, if the user causes a lip to contact the first optical waveguide 1114, a pressure may be applied to the first optical waveguide 114 formed of polymer, and thus a shape of the first optical waveguide 1114 formed of a polymer may be changed. Therefore, the first optical waveguide 1114 formed of a polymer may be directly coupled to the lip. The film 1110 including the first optical waveguide 1114 may include a polymer.

The first optical waveguide 1114 formed of a polymer may be replaced in the glucose measuring apparatus 1100 by being separated from the glucose measuring apparatus 1100 to be replaced with a new first optical waveguide formed of polymer after being used for a preset period. For example, the first optical waveguide 114 may be combined with or separated from the glucose measuring apparatus 1100, or the film 1110 including the first optical waveguide 1114 may be combined with or separated from the glucose measuring apparatus 1100.

If the first optical waveguide 1114 formed of polymer is replaceable, abrasion and sanitary problems caused by continuous use may be prevented. The user may also continuously use a main body of the glucose measuring apparatus 1100 and replace only the first optical waveguide 1114 so as to decrease maintenance costs.

The first optical waveguide 1114 may include a tapering waveguide 1140 having a thinly cut cladding. An evanescent wave may be further efficiently absorbed into the object by the thinly cut cladding, and a blood glucose level may be further precisely measured.

FIG. 11C illustrates an evanescent wave 1180 and an ATR-NIR 1190 in the first optical waveguide 1114.

An NIR irradiated by an NIR irradiator 1111 is propagated through a total reflection in the first optical waveguide 1114. The NIR 1190 advances from a core 1114 having a high refractive index toward a cladding 1160 having a low refractive index. A total reflection occurs if an incidence angle is greater than or equal to a threshold angle.

The evanescent wave 1180 refers to an NIR, a portion of which is propagated outside the core 1114 when a total reflection occurs. The evanescent wave 1180 may advance to a very shallow depth 1150 outside the core 1114.

If the evanescent wave 11180 is propagated outside the core 1114 to be absorbed into the object, a transmittance of a wavelength of the NIR 1190 that is completely reflected is less than that of a wavelength of a first NIR 1170 that is not completely reflected. Therefore, an NIR, a portion of which is absorbed into the object by the evanescent wave 1180 and which is propagated through a total reflection in the first optical waveguide 1114, is referred to as an ATR-NIR.

An analyzer may analyze the ATR-NIR 1190 and measure a blood glucose level based on an IR spectroscopy.

The glucose measuring apparatus 1100 according to the present embodiment may compare an ATR-NIR received from the first optical waveguide 1114 with a control NIR received from a second optical waveguide 1115 to further efficiently measure a blood glucose level.

The control NIR received from the second optical waveguide 1115 refers to an NIR that is not absorbed into the object and is propagated from the second optical waveguide 1115 through a complete reflection. Therefore, an ATR-NIR received from the second optical waveguide 1115 may be a control group, and an ATR-NIR received from the first optical waveguide 1114 may be an experimental group.

In detail, referring to FIG. 11B, the glucose measuring apparatus 1100 according to the present embodiment may include the second optical waveguide 1115, which is not close to the object. For example, the first optical waveguide 1114 may be positioned on an outer surface of the mouthpiece 1170, and the second optical waveguide 1115 may be is positioned in the mouthpiece 1170. Alternatively, the film 1110 may include includes the first and second optical waveguides 1114 and 1115, and the second optical waveguide 1115 may be is coated with a polymer so as to be separated from the object. Therefore, although an evanescent wave is generated, the control NIR received from the second optical waveguide 1115 does not include information about the object.

The NIR irradiator 1111 irradiates a portion of an NIR to the first optical waveguide 1114 and an other portion of the NIR to the second optical waveguide 1115, and freely controls a ratio between an NIR irradiated to the first optical waveguide 1114 and an NIR irradiated to the second optical waveguide 1115. The ATR-NIR received from the second optical waveguide 1115 corresponds to a control group, and thus the NIR irradiator 1111 irradiates a small amount of NIR to the second optical waveguide 1115. For example, the NIR irradiator 1111 irradiates 90% of an NIR to the first optical waveguide 1114 and 10% of the NIR to the second optical waveguide 1115.

NIR receivers 1112 and 1113 receive an ATR-NIR from the first optical waveguide 1114 and a control NIR from the second optical waveguide 1115.

The analyzer measures a blood glucose level based on an ATR-NIR and a complete reflection NIR.

Figure 12A:
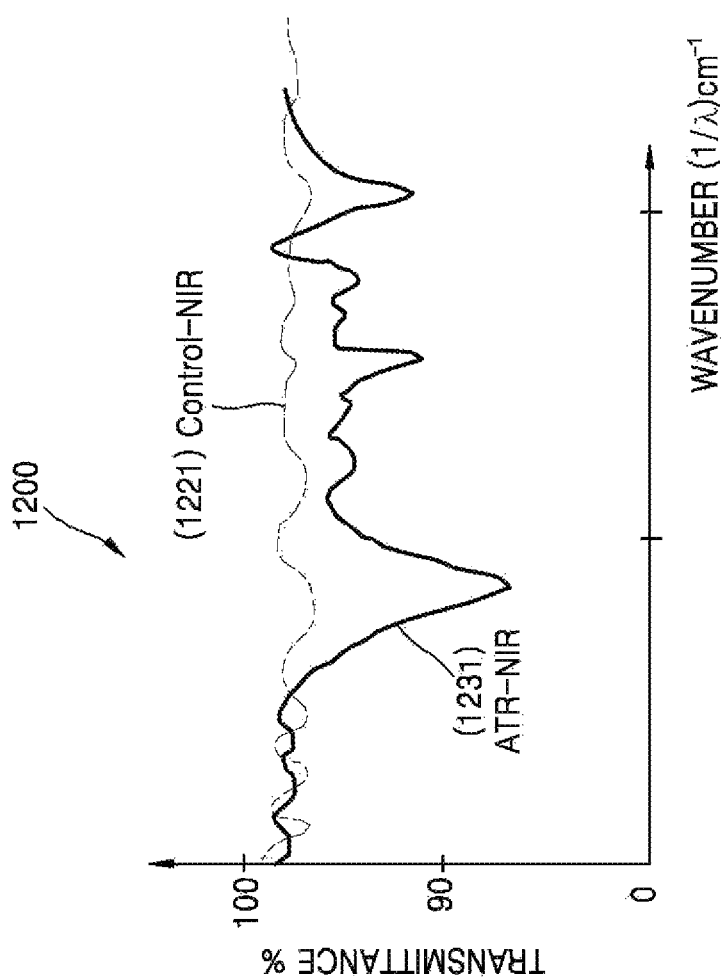
FIGS. 12A and 12B illustrate transmittances of an ATR-NIR received from a first optical waveguide and a control NIR received from a second optical waveguide, according to an embodiment of the present disclosure.
Figure 12B:
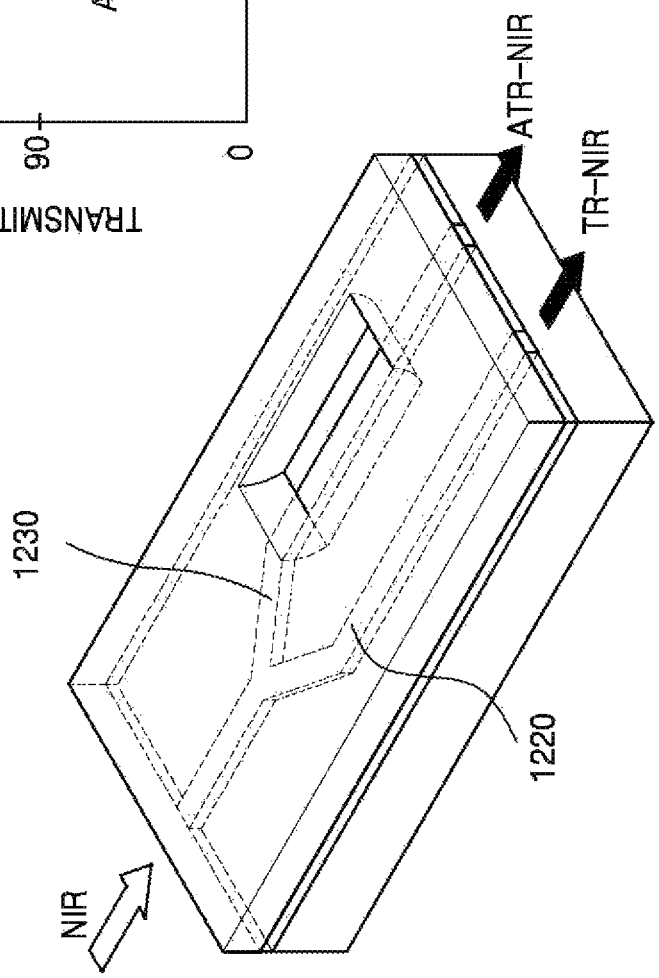

FIGS. 12A and 12B illustrate a transmittance of an ATR-NIR received from a first optical waveguide 1230 and a transmittance of a control NIR received from a second optical waveguide 1220, according to an embodiment of the present disclosure.

For example, in FIG. 12A, an analyzer further precisely measures a blood glucose level based on a difference between a transmittance 1221 of a control NIR and a transmittance 1231 of an ATR-NIR. The transmittance 1221 of the control NIR includes noise caused by an absorption of an NIR into a material except the object. Therefore, the transmittance 1231 of the ATR-NIR is subtracted from the transmittance 1221 of the control NIR to increase an SNR.

In FIG. 12B, the analyzer considers a ratio between an NIR irradiated to the first optical waveguide 1230 and an NIR irradiated to the second optical waveguide 1220 to calculate the difference between the transmittance 1221 of the control NIR and the transmittance 1231 of the ATR-NIR. For example, if an NIR irradiator irradiates 90% of an NIR to the first optical waveguide 1230 and 10% of the NIR to the second optical waveguide 1220, the analyzer nine-fold amplifies gain of the control NIR received from the second optical waveguide 1220 to calculate a difference of the control NIR from an ATR-NIR. As another example, if the NIR irradiator irradiates 50% of an NIR to the first optical waveguide 1230 and the other 50% of the NIR to the second optical waveguide 1220, the analyzer does not amplify the gain of the control NIR received from the second optical waveguide 1220 and may calculate the difference of the control NIR from the ATR-NIR.

FIGS. 13A, 13B and 13C illustrate structures of pressure measurers included in the glucose measuring apparatus 1100 of FIGS. 11A, 11B and 11C, according to an embodiment of the present disclosure.

FIG. 13A illustrates a film 1300 including a first optical waveguide 1330. The film 1300 of FIG. 13A may further include pressure measurers 1310 and 1320 in comparison with the film 1110 of FIG. 11B. Therefore, the same descriptions of the film 1300 as those of the film 1110 of FIG. 11B are omitted for conciseness.

FIG. 13B illustrates the pressure measurers 1310 and 1320 before an object is close to the film 1300. FIG. 13C illustrates the pressure measurers 1310 and 1320 after the object is close to the film 1300.

In comparison of the pressure measurers 1310 and 1320 of FIGS. 13A, 13B and 13C with the pressure measurers 1040 and 1050 of FIGS. 10A, 10B and 10C, the pressure measurers 1040 and 1050 of FIGS. 10A, 10B and 10C are positioned in the mouthpiece 1070. However, the pressure measurers 1310 and 1320 of FIGS. 13A, 13B and 13C are positioned in the film 1300.

Since the object is close to a first optical waveguide 1330, the glucose measuring apparatus 1100 may measure a pressure generated between the first optical waveguide 1330 and the object to control a start time of an NIR.

If a user causes the first optical waveguide 1330 to contact the object, the pressure generated between the object and the first optical waveguide 1330 may be applied to the elastic part 1310. As the pressure applied to the elastic part 1310 increases, the elastic part 1310 may gradually compress, and thus the switch 1320 may be connected.

If the pressure measured by the pressure measurers 1310 and 1320 is greater than or equal to a preset value, the NIR irradiator 1111 may irradiate an NIR to the object. For example, if the switch 1320 is turned on due to the compression of the elastic part 1310, the NIR irradiator 1111 may irradiate an NIR to the object.

Figure 14A:
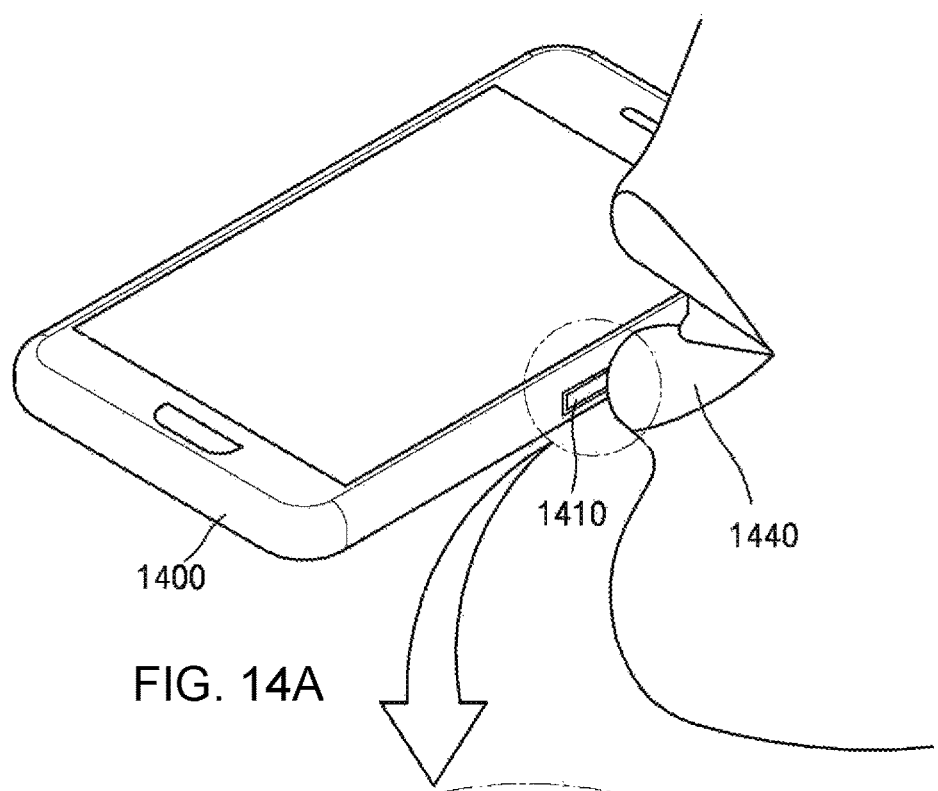
FIGS. 14A and 14B illustrate a glucose measuring apparatus that is combined with a portable device, according to another embodiment of the present disclosure.
Figure 14B:
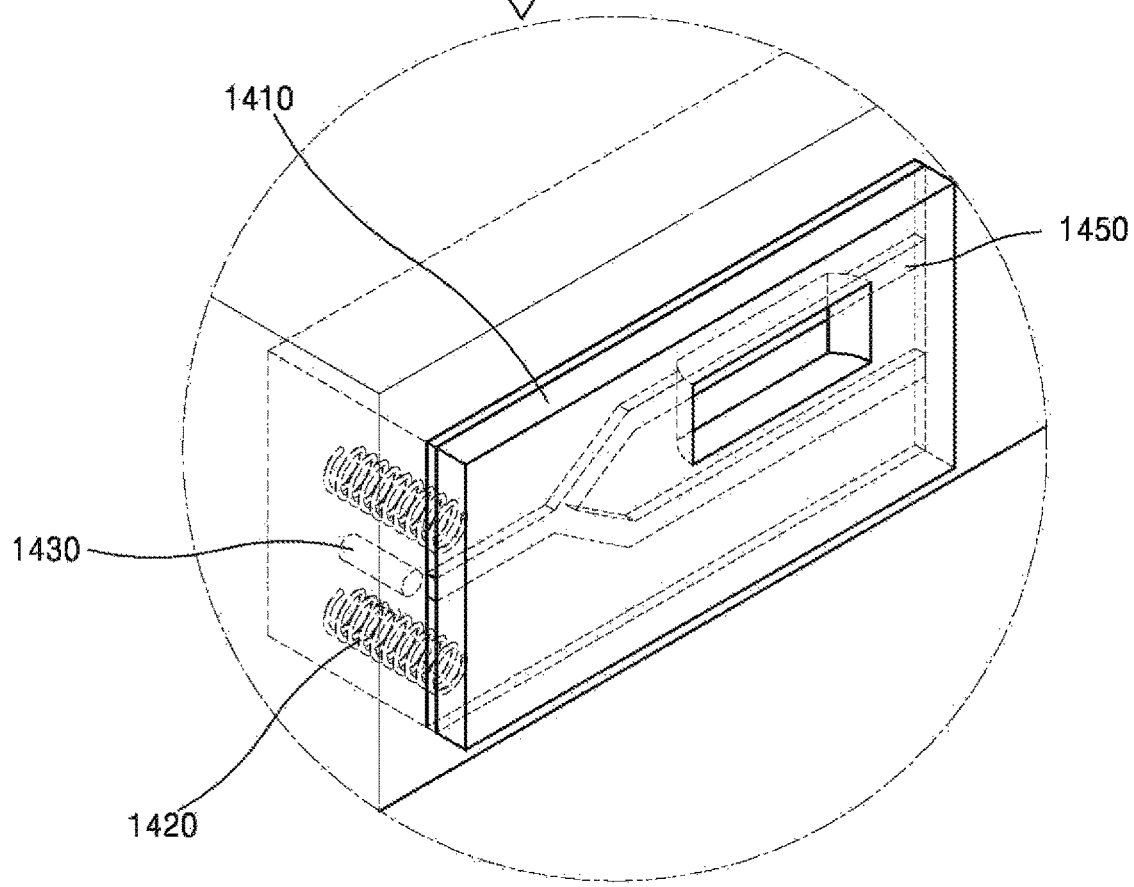

FIGS. 14A and 14B illustrate a glucose measuring apparatus 1410 that is combined with a portable device 1400, according to another embodiment of the present disclosure. Specifically, FIG. 14A illustrates an operation of the glucose measuring apparatus 1410 that is combined with the portable device 1400 and measures a blood glucose level, and FIG. 14B illustrates an enlarged view of the glucose measuring apparatus 1410 that is combined with the portable device 1400.

In FIG. 14A, the glucose measuring apparatus 1410 may be combined with the portable device 1400 such as a smartphone or a wearable device at a side of the portable device 1400.

The glucose measuring apparatus 1410 may include pressure measurers 1420 and 1430, an NIR irradiator, NIR receivers, and an analyzer. The pressure measurers 1420 and 1430 of FIG. 14B may correspond to the pressure measurers 950 and 960 of FIG. 9. Therefore, the same descriptions of the pressure measurers 1420 and 1430 as those of the pressure measurers 950 and 960 of FIG. 9B are omitted for conciseness.

For example, in FIG. 14A, if a user causes a lip 1440 to contact the glucose measuring apparatus 1410, a pressure generated between the lip 1440 and the glucose measuring apparatus 1410 is applied to the elastic part 1420. Due to a compression of the elastic part 1420, the switch 1430 may be connected, and the NIR irradiator may irradiate an NIR to a first optical waveguide 1450. The NIR receivers receive an ATR-NIR from the first optical waveguide 1450, and the analyzer analyzes a blood glucose level based on the received ATR-NIR.

Figure 15A:
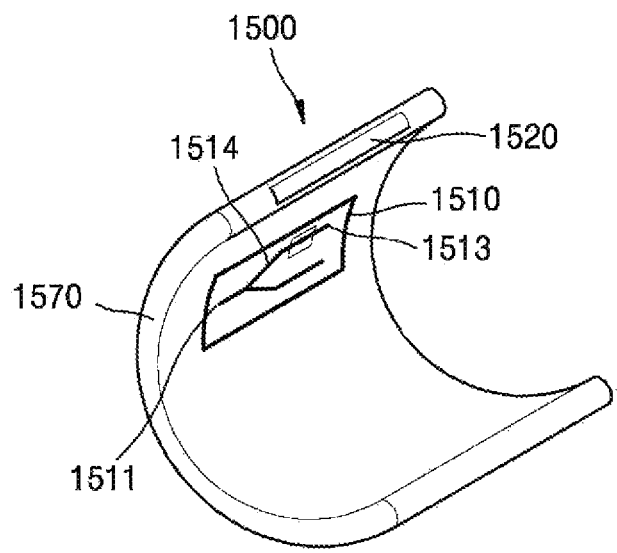
FIGS. 15A, 15B and 15C illustrate an operation of a glucose measuring apparatus that measures a blood glucose level of an object based on an NIR and an exhalation, according to an embodiment of the present disclosure.
Figure 15B:
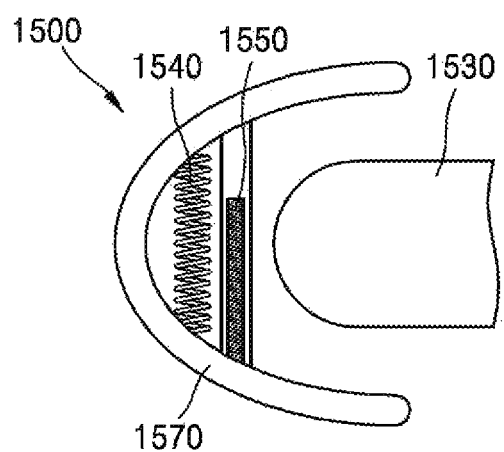
Figure 15C:
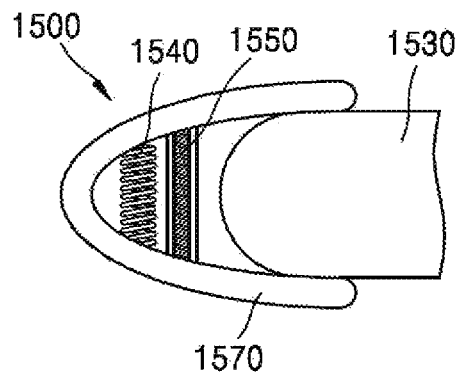

FIGS. 15A, 15B and 15C illustrate an operation of a glucose measuring apparatus 1500 that measures a blood glucose level based on an NIR and exhalation, according to an embodiment of the present disclosure.

The glucose measuring apparatus 1500 of FIGS. 15A, 15B and 15C further includes an exhalation duct 1520 in comparison with the glucose measuring apparatus 1000 of FIGS. 10A, 10B and 10C. The other elements of the glucose measuring apparatus 1500 of FIGS. 15A, 15B and 15C respectively correspond to the elements of the glucose measuring apparatus 1000 of FIGS. 10A, 10B and 10C. In detail, pressure measurers 1540 and 1550, an NIR irradiator 1511, an NIR receiver 1513, a first optical waveguide 1514, a film 1510, and a mouthpiece 1570 of the glucose measuring apparatus 1500 of FIGS. 15A, 15B and 15C may respectively correspond to the pressure measurers 1040 and 1050, the NIR receiver 1011, the NIR receiver 1013, the first optical waveguide 1014, the film 1510, and the mouthpiece 1070 of the glucose measuring apparatus 1000 of FIGS. 10A, 10B and 10C. Therefore, the same descriptions of these aspects of the glucose measuring apparatus 1500 of FIGS. 15A, 15B and 15C as those of the glucose measuring apparatus 1000 of FIGS. 10A, 10B and 10C are omitted for conciseness.

The glucose measuring apparatus 1500 according to the present embodiment may further efficiently measure a blood glucose level based on an NIR and exhalation.

Specifically, the mouthpiece 1570 may include the exhalation duct 1520 through which exhalation passes. For example, a user may hold the mouthpiece 1570 in a mouth of the user and cause a lip 1530 contact the first optical waveguide 1514 and exhalation to flow into the exhalation duct 1520.

An analyzer may include a spectroscope and an exhalation analyzer to analyze a combination of an NIR and exhalation.

That is, the exhalation analyzer may receive the exhalation of the user through the exhalation duct 1520 and analyze a concentration of acetone or ketone included in the exhalation of the user. For example, an exhalation of a diabetic may include acetone due to a partial oxidation of fat, and thus a high concentration of acetone may indicate severe diabetes. The exhalation analyzer may additionally monitor several types of gases to increase a correlation between a gas concentration and diabetes. Therefore, the exhalation analyzer may measure a blood glucose level based on acetone included in an exhalation and concentrations of other gases.

If a pressure measured by the pressure measurers 1540 and 1550 is greater than or equal to a preset value, the NIR irradiator 1511 irradiates an NIR to the first optical waveguide 1514.

The NIR receiver 1513 receives an ATR-NIR from the first optical waveguide 1514.

The spectroscope analyzes the NIR received by the NIR receiver 1513 based on an IR spectroscopy.

Figure 16:
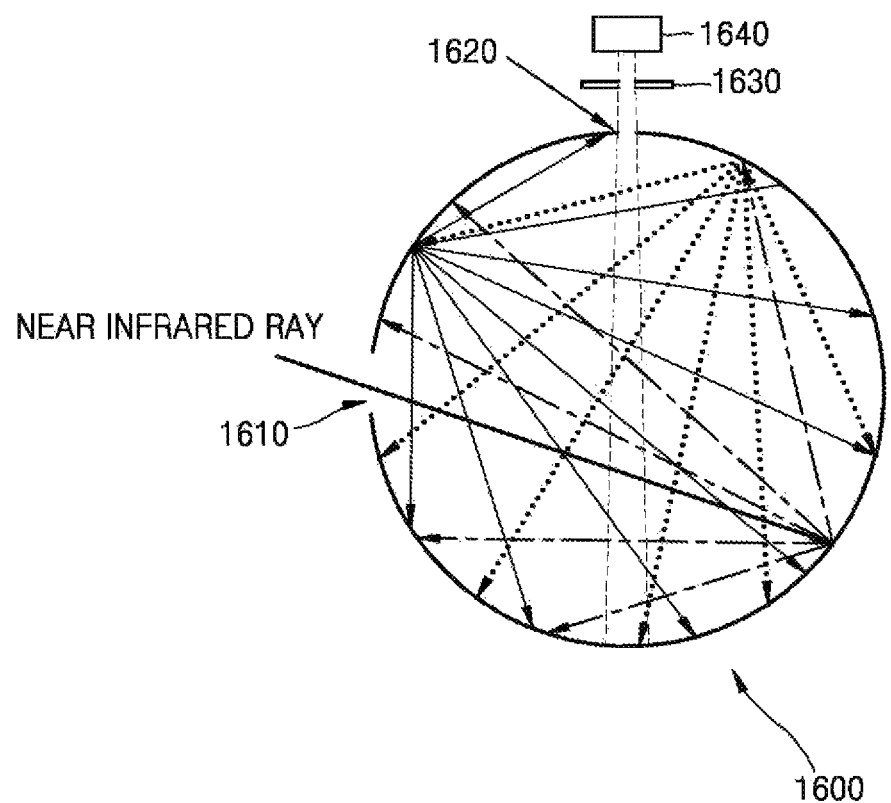
FIG. 16 illustrates an integrating sphere included in an NIR receiver, according to an embodiment of the present disclosure.

FIG. 16 illustrates an integrating sphere included in an NIR receiver according to an embodiment of the present disclosure.

The NIR receiver may include an integrating sphere 1600 that collects NIRs. The integrating sphere 1600 may intensively collect received NIRs at one place based on reflections and scattering of the NIRs. The integrating sphere 1600 may be used in both of an absorption mode and an ATR mode.

At least one of an NIR reflected or scattered from an object, an NIR penetrating through the object, and an NIR propagated through a first optical waveguide is propagated into the integrating sphere 1600 through a collection port. NIRs are reflected and scattered in the integrating sphere 1600 according to incidence angles and propagated to the outside through a detection port 1620. The NIRs propagated to the outside through the detection port 1620 are collected at a detector 1640 through an aperture 1630.

The integrating sphere 1600 is efficient when an amount or gain of an NIR received by the NIR receiver is not sufficient. Analyzers may further efficiently measure a blood glucose level through the NIRs collected at the detector 1640.

Figure 17B:
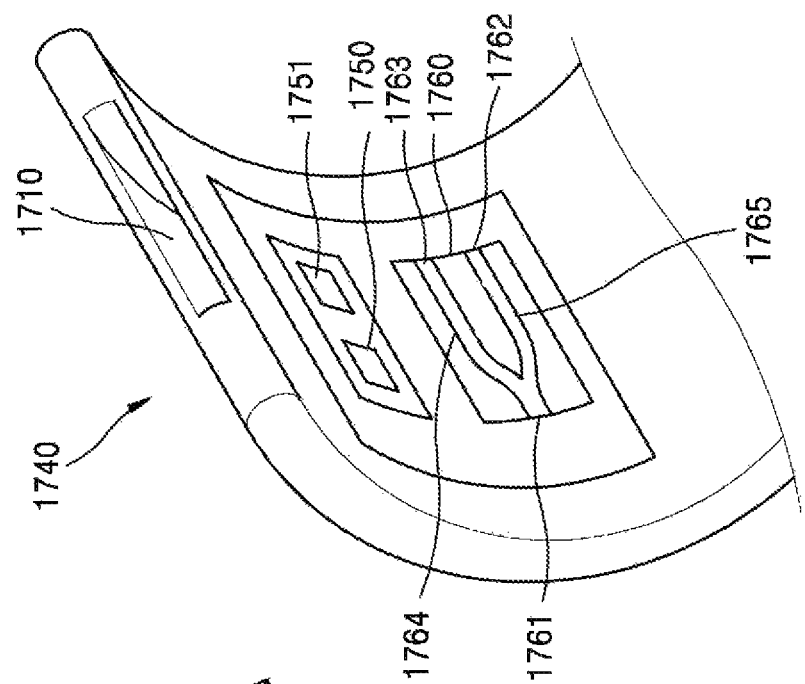
FIGS. 17A and 17B illustrate an operation of a glucose measuring apparatus that measures a blood glucose level of an object based on an NIR and an exhalation, according to another embodiment of the present disclosure.
Figure 17A:
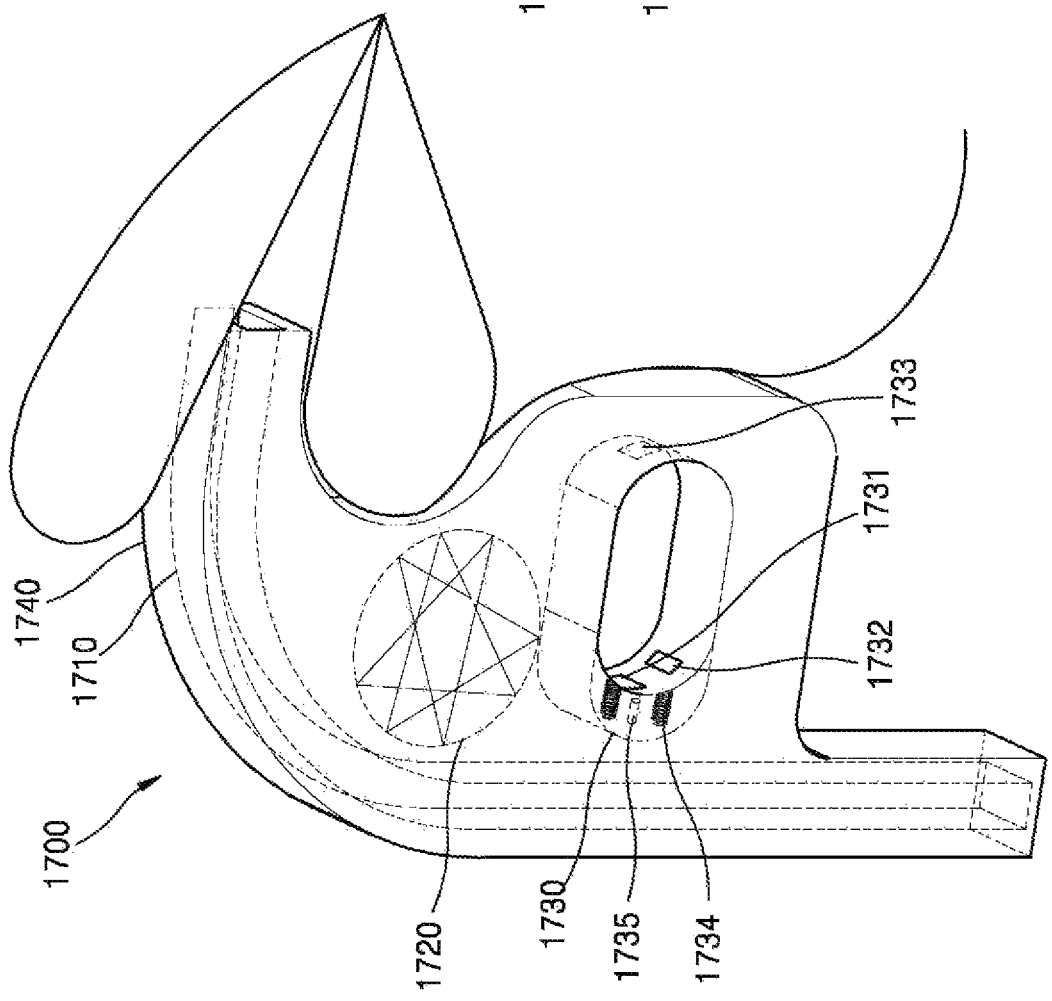

FIGS. 17A and 17B illustrate an operation of a glucose measuring apparatus 1700 that measures glucose based on an NIR and exhalation according to another embodiment of the present disclosure.

The glucose measuring apparatus 1700 may measure a blood glucose level based on exhalation. For example, the glucose measuring apparatus 1700 receives exhalation of a user through a mouthpiece 1740 including an exhalation duct 1710, and an exhalation analyzer may measure a blood glucose level based on a concentration of acetone or ketone included in the exhalation.

As shown in FIG. 17B, the glucose measuring apparatus 1700 may irradiate an NIR to a lip or a tongue to measure a blood glucose level. The glucose measuring apparatus 1700 may include a first NIR irradiator 1750 and a first NIR receiver 1751. The first NIR irradiator 1750 may be positioned on a mouthpiece 1740, which is close to the lip or the tongue, to directly irradiate an NIR to the lip, and the first NIR receiver 1751 may be positioned on the mouthpiece 1740, which is close to the lip or the tongue, to receive the NIR reflected from the lip. If a pressure measured by a first pressure measurer is greater than or equal to a preset value, the first NIR irradiator 1750 irradiates an NIR to the lip or the tongue. The first pressure measurer may include an elastic part or a pressure sensor as described above with reference to FIGS. 6A through 9C. A spectroscope may measure a blood glucose level based on the NIR received by the first NIR receiver 1751.

The glucose measuring apparatus 1700 may measure the blood glucose level based on an ATR-NIR and may include a first optical waveguide 1764 positioned on the mouthpiece 1740 to be close to the lip or the tongue. The glucose measuring apparatus 1700 may also include a film 1760 including the first optical waveguide 1764, a second NIR irradiator 1761 that irradiates an NIR to the first optical waveguide 1764, and second NIR receivers 1762 and 1763 that receive the NIR from the first optical waveguide 1764. If a pressure measured by a pressure measurer is greater than or equal to a preset value, the second NIR irradiator 1761 irradiates an NIR to the first optical waveguide 1764. The pressure measurer may include an elastic part or a pressure sensor as described above with reference to FIGS. 10A, 10B and 15C. The spectroscope may measure a blood glucose level based on the NIR received by the NIR receiver 1751.

As another example in FIG. 17A, the glucose measuring apparatus 1700 may irradiate an NIR to a finger to measure a blood glucose level. The glucose measuring apparatus 1700 may include a trigger 1730, a third NIR irradiator 1731, and third NIR receivers 1732 and 1733. The trigger 1730 may be a housing of the glucose measuring apparatus 1700 that may be pulled with a finger or contact the finger. The trigger 1730 may also include third pressure measurers 1734 and 1735 including the elastic part 1734 that receives a pressure generated between the trigger 1730 and the finger when a user pulls the trigger 1730 with the finger. The third pressure measurers 1734 and 1735 may also measure the pressure the elastic part 1734 receives. For example, the third pressure measurers 1734 and 1735 may include the switch 1735 that is turned on if the pressure the elastic part 1734 receives is greater than or equal to a preset value.

If the pressure measured by the third pressure measurers 1734 and 1735 is greater than or equal to the preset value, the third NIR irradiator 1731 irradiates an NIR to the finger. The NIR receiver 1732 may receive the NIR reflected from the finger. Alternatively, the NIR receiver 1733 may receive the NIR that penetrates through the finger. The spectroscope may measure a blood glucose level based on the NIR received by the NIR receivers 1732 and 1733.

The glucose measuring apparatus 1700 may include an integrating sphere 1720 that intensively collects received NIRs at one location based on reflections and scattering of the NIRs. The integrating sphere 1720 may be used in both of an absorption mode and an ATR-NIR mode.

FIG. 18 illustrates a method 1800 of measuring glucose according to an embodiment of the present disclosure.

The method 1800 has some of the same steps as those described in reference to the glucose measuring apparatuses 400a and 500. Therefore, the same descriptions of the method 1800 as those of FIGS. 1 through 17 are omitted for conciseness.

Referring to FIG. 18, in step 1810, a pressure applied to an object is measured. That is, a pressure an elastic part receives may be measured or a pressure may be measured through a pressure sensor. Step 1810 may be performed by the pressure measurers 410a and 510.

The method 1800 may further include directly applying the pressure to the object by use of the pressurizer 880.

In step 1820, a determination is made as to whether the measured pressure is greater than or equal to a preset value. If it is determined in step 1820 that the measured pressure is less than the preset value, the method returns to step 1810 and the pressure applied to the object is re-measured.

If it is determined in step 1820 that the measured pressure is greater than or equal to the preset value, an NIR is irradiated to the object in step 1830. A wavelength of the NIR may be between about 0.8 µm and about 1.8 µm. Steps 1820 and 1830 may be performed by the NIR irradiators 420a and 520.

In step 1840, at least one of an NIR reflected from the object, a scattered NIR, and an NIR penetrating through the object is received. Step 1840 may be performed by the NIR receivers 430a and 530.

In step 1850, a blood glucose level is measured based on the received NIR. In detail, in the method 1800, the received NIR may be analyzed, and the blood glucose level may be measured based on an IR spectroscopy. Step 1850 may be performed by the analyzers 440a and 540.

Figure 19:
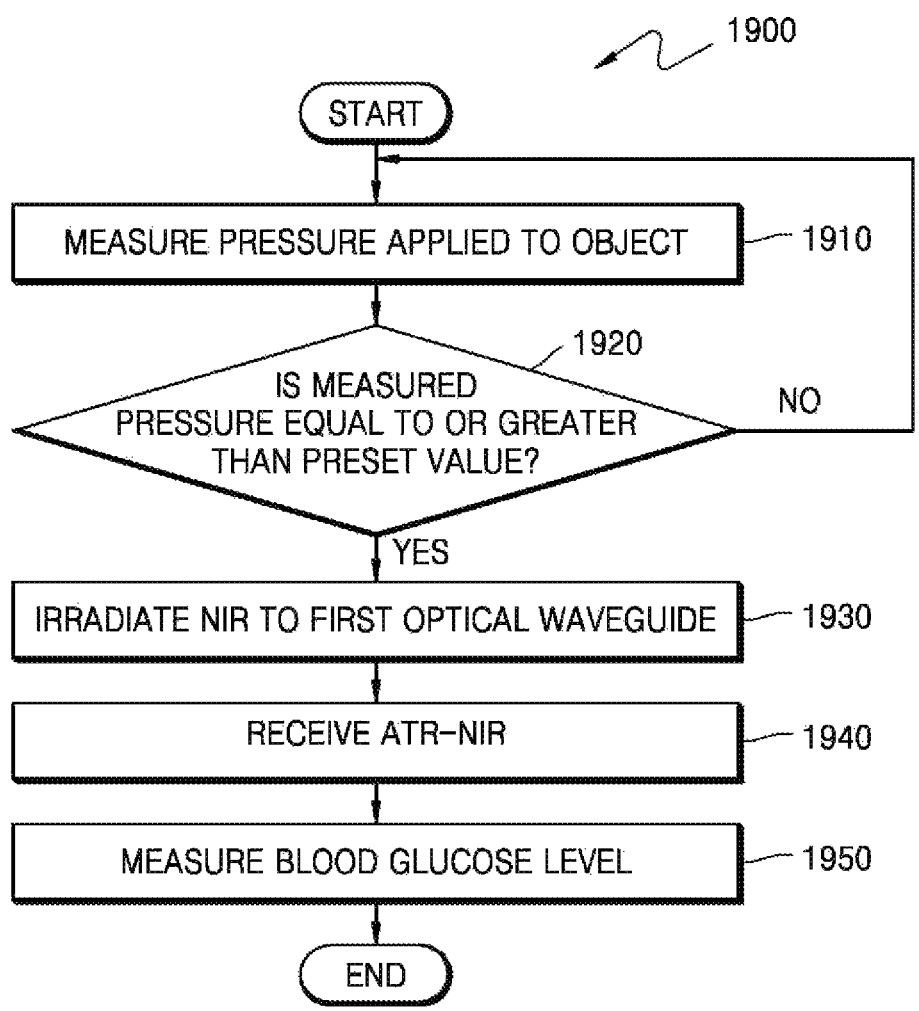
FIG. 19 is a flowchart of a glucose measuring method according to another embodiment of the present disclosure.

FIG. 19 illustrates a method 1900 of measuring glucose according to another embodiment of the present disclosure.

The method 1900 has some of the same steps as those described in reference to the glucose measuring apparatus 400b and 500. Therefore, the same descriptions of the method 1900 as those of FIGS. 1 through 17 are omitted for conciseness.

Referring to FIG. 19, in step 1910, a pressure applied to an object is measured. That is, a pressure an elastic part receives may be measured or a pressure may be measured through a pressure sensor. Step 1910 may be performed by the pressure measurers 410b and 510.

If it is determined in step 1920 that the measured pressure is greater than or equal to a preset value, an NIR is irradiated to a first optical waveguide close to the object in step 1930. The first optical waveguide may include polymer such as at least one of PMMA, PS, and PC. The first optical waveguide may be replaceable in a glucose measuring apparatus. The first optical waveguide may also include a tapering waveguide. Step 1930 may be performed by the NIR irradiators 420b and 520.

In step 1940, an ATR-NIR is received from the first optical waveguide. Step 1940 may be performed by the NIR receivers 430b and 530.

In step 1950, a blood glucose level is measured based on the ATR-NIR received in step 1940. Step 1950 may be performed by the analyzers 440b and 540.

Figure 20:
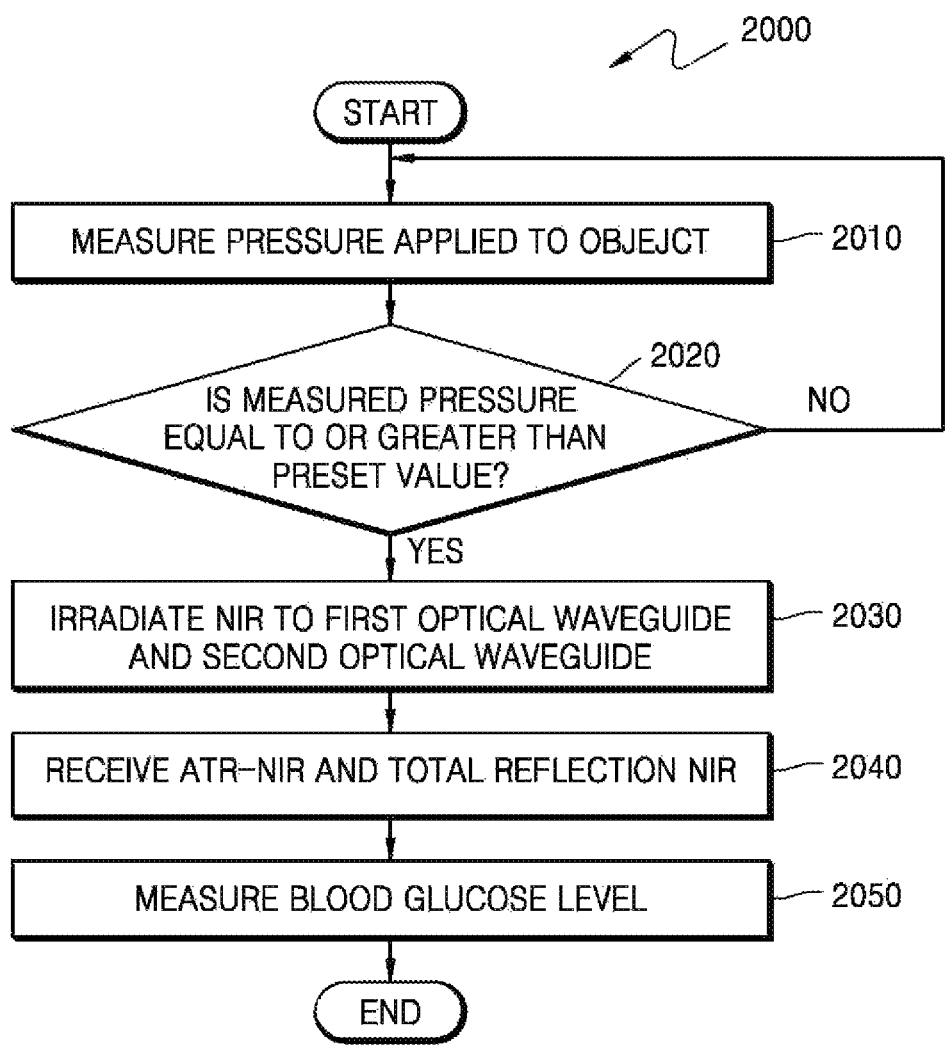
FIG. 20 is a flowchart of a glucose measuring method according to another embodiment of the present disclosure.

FIG. 20 illustrates a method 2000 of measuring glucose according to another embodiment of the present disclosure.

Most of steps 2010 and 2020 respectively correspond to steps 1910 and 1920, and thus a description thereof will be omitted for conciseness.

If it is determined in step 2020 that a measured pressure is greater than or equal to a preset value, a portion of an NIR is irradiated to a first optical waveguide close to an object, and an other portion of the NIR is irradiated to a second optical waveguide that is away from the object, in step 2030.

Step 2040 includes receiving an ATR-NIR from the first optical waveguide and a control NIR from the second optical waveguide, and is performed by the NIR receivers 430b and 530.

In step 2050, a blood glucose level is measured based on the ATR-NIR and the control NIR by the analyzers 440b and 540.

According to a glucose measuring apparatus and a glucose measuring method according to embodiments of the present disclosure, noise made by body components except glucose and errors occurring due to an external pressure may be reduced and a blood glucose level is more accurately measured.

The blood glucose level of the present disclosure is further efficiently measured based on an IR and exhalation.

Embodiments of the present disclosure may be written as computer programs and may be implemented in general-use digital computers that execute the programs using a non-transitory computer readable recording medium.

Examples of the computer readable recording medium include magnetic storage media such as ROM, floppy disks, and hard disks, etc, and optical recording media such as CD-ROMs or DVDs.

While one or more embodiments have been described with reference to the figures, it will be understood by those of ordinary skill in the art that various changes in form and details may be made therein without departing from the spirit and scope of the present disclosure. Therefore, the scope of the present disclosure should not be defined as being limited to the embodiments, but should be defined by the appended claims and equivalents thereof.

What is claimed is:

1. A glucose measuring apparatus comprising:
a pressure measurer, including an elastic part or a pressure sensor, that measures a pressure applied to an object;
a film that comprises a first optical waveguide configured to be close to the object;
a near infrared ray (NIR) irradiator that irradiates an NIR to the first optical waveguide if the measured pressure is greater than or equal to a preset value;
an NIR receiver that receives an attenuated total reflection NIR (ATR-NIR) from the first optical waveguide; and
an analyzer that measures a blood glucose level based on the ATR-NIR,
wherein the film is an independent module that can be combined with and separated from the glucose measuring apparatus.

2. The glucose measuring apparatus of claim 1,
wherein a wavelength of the NIR is between 0.8 microns (μm) and 1.8 μm.

3. The glucose measuring apparatus of claim 1, wherein, when the pressure measurer includes the elastic part, the elastic part receives the pressure applied to the object, and the pressure measurer further measures the pressure received by the elastic part.

4. The glucose measuring apparatus of claim 1, further comprising:
a pressurizer including a hinge that applies the pressure to the object.

5. The glucose measuring apparatus of claim 1,
wherein the glucose measuring apparatus has an identical shape to a shape of the mouthpiece.

6. The glucose measuring apparatus of claim 1,
wherein the NIR receiver comprises an integrating sphere that collects the received NIR.

7. The glucose measuring apparatus of claim 1,
wherein the first optical waveguide comprises a polymer.

8. The glucose measuring apparatus of claim 7,
wherein the polymer comprises at least one of polymethyl methacrylate (PMMA), poly styrene (PS), and polycarbonate (PC).

9. The glucose measuring apparatus of claim 7,
wherein the first optical waveguide is replaceable in the glucose measuring apparatus.

10. The glucose measuring apparatus of claim 1,
wherein the first optical waveguide comprises a tapered waveguide.

11. A method of measuring a blood glucose level in a glucose measuring apparatus, the method comprising:
measuring a pressure applied to an object by positioning a film that comprises a first optical waveguide close to the object;
if the pressure is greater than or equal to a preset value, irradiating a near infrared ray (NIR) to the first optical waveguide;
receiving an attenuated total reflection NIR (ATR-NIR) from the first optical waveguide; and
measuring a blood glucose level based on the ATR-NIR,
wherein the film including the first optical waveguide is an independent module that can be combined with and separated from the glucose measuring apparatus.

12. The method of claim 11,
wherein the first optical waveguide comprises a polymer.

13. A computer program product comprising a non-transitory computer-readable storage medium configured to store one or more computer programs including instructions that, when executed by at least one processor, cause the at least one processor to control to perform a method of measuring a blood glucose level in a glucose measuring apparatus, the method comprising:
measuring a pressure applied to an object by positioning a film that comprises a first optical waveguide close to the object;
if the pressure is greater than or equal to a preset value, irradiating a near infrared ray (NIR) to the first optical waveguide;
receiving an attenuated total reflection NIR (ATR-NIR) from the first optical waveguide; and
measuring a blood glucose level based on the ATR-NIR, wherein the film including the first optical waveguide is an independent module that can be combined with and separated from the glucose measuring apparatus.

* * * * *